(12) United States Patent
Kasputis et al.

(10) Patent No.: US 10,973,956 B2
(45) Date of Patent: Apr. 13, 2021

(54) MICROPOROUS HYDROGEL SCAFFOLDS FOR CELL TRANSPLANTATION

(71) Applicant: THE REGENTS OF THE UNIVERSITY OF MICHIGAN, Ann Arbor, MI (US)

(72) Inventors: Tadas Kasputis, Ann Arbor, MI (US); Michael Skoumal, Ann Arbor, MI (US); Lonnie D. Shea, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 16 days.

(21) Appl. No.: 15/863,843

(22) Filed: Jan. 5, 2018

(65) Prior Publication Data
US 2018/0185550 A1 Jul. 5, 2018

Related U.S. Application Data

(60) Provisional application No. 62/442,768, filed on Jan. 5, 2017.

(51) Int. Cl.
| | | |
|---|---|---|
| *A61L 27/56* | (2006.01) | |
| *A61L 27/18* | (2006.01) | |
| *A61L 27/24* | (2006.01) | |
| *A61L 27/54* | (2006.01) | |
| *A61L 27/38* | (2006.01) | |
| *A61L 27/22* | (2006.01) | |
| *A61L 27/36* | (2006.01) | |

(52) U.S. Cl.
CPC .............. *A61L 27/56* (2013.01); *A61L 27/18* (2013.01); *A61L 27/222* (2013.01); *A61L 27/24* (2013.01); *A61L 27/3633* (2013.01); *A61L 27/38* (2013.01); *A61L 27/3804* (2013.01); *A61L 27/54* (2013.01); *A61L 2300/414* (2013.01); *A61L 2300/43* (2013.01)

(58) Field of Classification Search
None
See application file for complete search history.

(56) References Cited

U.S. PATENT DOCUMENTS

| | | | |
|---|---|---|---|
| 5,514,378 A | 5/1996 | Mikos et al. | |
| 5,965,125 A | 10/1999 | Mineau-Hanschke | |
| 7,361,334 B2 * | 4/2008 | Latta | A61P 19/02 424/93.1 |
| 7,427,602 B1 | 9/2008 | Shea et al. | |
| 7,611,728 B2 | 11/2009 | Kidane et al. | |
| 2011/0296538 A1 | 12/2011 | Segall et al. | |
| 2014/0072510 A1 | 3/2014 | Shea et al. | |
| 2015/0283073 A1 | 10/2015 | Tang | |

FOREIGN PATENT DOCUMENTS

| | | |
|---|---|---|
| WO | WO-2011/053940 A2 | 5/2011 |
| WO | WO-2017/120486 A1 | 7/2017 |
| WO | WO-2018/165432 A1 | 9/2018 |

OTHER PUBLICATIONS

Weber, Laney M; Anseth, Kristi S; "Hydrogel encapsulation environments functionalized with extracellular matrix interactions increase islet insulin secretion" Matrix Biology, 27, 667-673, 2008 (Year: 2008).*
Phelps, Edward A; et al; "Engineered VEGF-releasing PEG-MAL hydrogel for pancreatic islet vascularization" Drug Delivery and Translational Research, 5, 125-136, 2015 (Year: 2015).*
Xu, Gang; et al; "Exendin-4 Stimulates Both [beta]-Cell Replication and Neogenesis, Resulting in Increased [beta]-Cell Mass and Improved Glucose Tolerance in Diabetic Rats" Diabetes, 48, 2270-2276, 1999 (Year: 1999).*
Wong, Adrianne L; et al; "Surrogate insulin-producing cells" F1000 Medicine Reports, 4, 1-9, 2012 (Year: 2012).*
Attali et al., "Control of β-Cell Differentiation by the Pancreatic Mesenchyme," Diabetes 56:1248-1258 (2007).
Avilés et al., "Hydrogels to modulate lentivirus delivery in vivo from microporous tissue engineering scaffolds," Drug Delivery and Translational Research. 1:91-101 (2011).
Baertschiger et al., "Mesenchymal Stem Cells Derived from Human Exocrine Pancreas Express Transcription Factors Implicated in Beta-Cell Development," Pancreas 37:75-84 (2008).
Barton et al., "Improvement in Outcomes of Clinical Islet Transplantation: 1999-2010," Diabetes Care 35: 1436-1445 (2012).
Bianchi et al., "Effects of Islet Transplantation and Mesenchymal Stem Cell Co-Transplantation in the Protection of Diabetic Neuropathy in Streptozotocin-Induced Diabetic Rats," Abstract, Journal of the Peripheral Nervous System 19:S3 (2014).
Blomeier et al., "Polymer Scaffolds as Synthetic Microenvironments for Extrahepatic Islet Transplantation," Transplantation 82:452-459 (2006).
Boehler et al., "A PLG/HAp composite scaffold for lentivirus delivery," Biomaterials 34:5431-5438 (2013).
Boehler et al., "Lentivirus Delivery of IL-10 to Promote and Sustain Machrophage Polarization Towards an Anti-Inflammatory Phenotype," Biotechnology and Bioengineering 111(6):1210-1221 (2014).
Boehler et al., "tissue engineering tools for modulation of the immune response," BioTechniques. 51(4):239-240 (2011).
Borowiak et al., "Small molecules efficienty direct endodermal differentiation of mouse and human embryonic stem cells," Cell Stem Cell. 4:348-358 (2009).
Bruin et al., "Maturation and function of human embryonic stem cell-derived pancreatic progenitors in macroencapsulation devices following transplant into mice," Diabetologia 56(9):1987-1998 (2013).
Chen et al., "A small molecule that directs differentiation of human ESCs into the pancreatic lineage," Nat Chem Biol. 5:258-265 (2009).

(Continued)

*Primary Examiner* — David W Berke-Schlessel
(74) *Attorney, Agent, or Firm* — Marshall, Gerstein & Borun LLP

(57) ABSTRACT

The present disclosure relates generally to biomaterial implants and methods for delivering a cell to an individual in need thereof and, more particularly, to biomaterial implants and techniques for delivering islets and/or β-cell progenitors to an individual.

13 Claims, 26 Drawing Sheets
(13 of 26 Drawing Sheet(s) Filed in Color)

(56) References Cited

OTHER PUBLICATIONS

Chen et al., "De Novo Formation of Insulin-Producing "Neo-β Cell Islets" from Intestinal Crypts," Cell Reports. 6:1046-1058 (2014).
Citro et al., "Anti-Inflammatory Strategies to Enhance Islet Engraftment and Survival," Current Diabetes Reports 13:733-744 (2013).
Duncan et al., "Dynamic Transcription Factor Activity Profiles Reveal Key Regulatory Interactions During Megakaryocytic and Erythroid Differentiation," Biotechnology and Bioengineering. 111(10):2082-2094 (2014).
Duvillie et al., "The Mesenchyme Controls the Timing of Pancreatic β-Cell Differentiation," Diabetes. 55:582-589 (2006).
Gangemi et al., "Islet Transplantation for Brittle type 1 Diabetes: The UIC Protocol," Am J Transplant. 8:1250-1261 (2008).
Gao et al., "Foxa2 Controls Vesicle Docking and Insulin Secretion in Mature β Cells," Cell Metabolism. 6:267-279 (2007).
Gibly et al., "Extrahepatic islet transplantation with microporous polymer scaffolds in syngeneic mouse and allogeneic porcine models," Biomaterials. 32:9677-9684 (2011).
Gibly et al., "Porous Scaffolds Support Extrahepatic Human Islet Transplantation, Engraftment and Function in Mice," Cell Transplant. 22:811-819 (2013).
Gower et al., "Biomaterial Scaffolds for Controlled, Localized Gene Delivery of Regenerative Factors," Adv Wound Care 2(3):100-106 (2013).
Gower et al., "Modulation of leukocyte infiltration and phenotype in microporous tissue engineering scaffolds via vector induced IL-10 expression," Biomaterials. 35(6):2024-2031 (2014).
Gradwohl et al., "neurogenin3 is required for the development of the four endocrine cell lineages of the pancreas," PNAS 97(4):1607-1611 (2000).
Graham et al., "PLG Scaffold Delivered Antigen-Specific Regulatory T Cells Induce Systemic Tolerance in Autoimmune Diabetes," Tissue Engineering Part A 19(11-12):1465-1475 (2013).
Hlavaty et al., "Enhancing Human Islet Transplantation by Localized Release of Trophic Factors From PLG Scaffolds," Am J Transplant. 14(7):1523-1532 (2014).
Jang et al., "Intramuscular delivery of DNA releasing microspheres: Microsphere properties and transgene expression," J Control Release. 112(1):120-128 (2006).
Jang et al., "Surface adsorption of DNA to tissue engineering scaffolds for efficient gene delivery," J Biomed Mater Res A. 77(1):50-58 (2006).
Jang et al., "Gene delivery from polymer scaffolds for tissue engineering," Expert Review of Medical Devices 1:127-38 (2004).
Jhala et al., "cAMP promotes pancreatic β-cell survival via CREB-mediated induction of IRS2," Genes & Development. 17:1575-1580 (2003).
Kelly et al., "Cell-surface markers for the isolation of pancreatic cell types derived from human embryonic stem cells," Nat Biotechnol. 29:750-756 (2011).
Kheradmand et al., "Permanent Protection of PLG Scaffold Transplanted Allogeneic Islet Grafts in Diabetic Mice Treated with ECDI-fixed Donor Splenocyte Infusions," Biomaterials. 32(20):4517-4524 (2011).
Krizik et al., "PDX-1 and Msx-2 expression in the regenerating and developing pancreas," Journal of Endocrinology 163:523-530 (1999).
Kroon et al., "Pancreatic endoderm derived from human embryonic stem cells generates glucose-responsive insulin-secreting cells in vivo," Nat Biotechnol. 26(4):443-452 (2008).
Lammert et al., "Induction of Pancreatic Differentiation by Signals from Blood Vessels," Science 294:564-567 (2001).
Lammert et al., "Role of endothelial cells in early pancreas and liver development," Mech Dev. 120:59-64 (2003).
Lammert et al., "Role of VEGF-A in Vascularization of Pancreatic Islets," Curr Biol. 13:1070-1074 (2003).
Landsman et al., "Pancreatic Mesenchyme Regulates Epithelial Organogenesis throughout Development," Plos Biology. 9(9):1-14 (2011).
Lee et al., "Foxa2 Controls Pdx1 Gene Expression in Pancreatic β-Cells In Vivo," Diabetes 51:2546-2551 (2002).
Liu et al., "Biomaterials Transforming growth factor-beta 1 delivery from microporous scaffolds decreases inflammation post-implant and enhances function of transplanted islets," Biomaterials. 80:11-19 (2016).
Lu et al., "Pancreatic β-Cell-specific Repression of Insulin Gene Transcription by CCAAT/Enhancer-binding Protein β," Journal of Biological Chemistry. 272:28349-28359 (1997).
Moberg, "The Role of the Innate Immunity in Islet Transplantation," Upsala Journal of Medical Sciences 110:17-56 (2005).
Ozmen et al., "Inhibition of Thrombin Abrogates the Instant Blood-Mediated Inflammatory Reaction Triggered by Isolated Human Islets," Diabetes. 51:1779-1784 (2002).
Pagliuca et al., "Generation of functional human pancreatic β cells in vitro," Cell 159:428-439 (2014).
Pagliuca et al., "How to make a functional β-cell," Development 140:2472-2483 (2013).
Park et al., "Exendin-4 Uses Irs2 Signaling to Mediate Pancreatic β Cell Growth and Function," The Journal of Biological Chemistry 281(2):1159-1168 (2006).
Pauls et al., "Function and regulation of zebrafish nkx2.2a during development of pancreatic islet and ducts," Developmental Biology 304:875-890 (2007).
Qi et al., "Implementation of a Simplified Method of Islet Isolation for Allogeneic Islet Transplantation in Cynomolgus Monkeys," Pancreas 43:226-235 (2014).
Qin et al., "Systematic Comparison of Constitutive Promoters and the Doxycycline-Inducible Promoter," Plos One 5(5):1-4 (2010).
Rao et al., "Enhanced Survival with Implantable Scaffolds That Capture Metastatic Breast Cancer Cells In Vivo," Cancer Research 76:5209-5218 (2016).
Rezania et al., "Enrichment of Human Embryonic Stem Cell-Derived NKX6.1-Expressing Pancreatic Progenitor Cells Accelerates the Maturation of Insulin-Secreting Cells In Vivo," Stem Cells 31(11):2432-2442 (2013).
Rezania et al., "Maturation of Human Embryonic Stem Cell-Derived Pancreatic Progenitors Into Functional Islets Capable of Treating Pre-Existing Diabetes in Mice," Diabetes 61:2016-2029 (2016).
Rezania et al., "Reversal of diabetes with insulin-producing cells derived in vitro from human pluripotent stem cells," Nature Biotechnology. 32(11):1121-1133 (2014).
Rios, "Encapsulating and Microporous Hydrogel-Based Platforms for Islet Transplantation and Fertility Preservation" A Dissertation (2016).
Rives et al. "Layered PLG Scaffolds for In Vivo Plasmid Delivery," Biomaterials 30(3):394-401 (2009).
Salvay et al., "Extracellular Matrix Protein-Coated Scaffolds Promote the Reversal of Diabetes After Extrahepatic Islet Transplanatation," Transplantation 85(10):1456-1464 (2008).
Salvay et al., "Gene delivery by surface immobilization of plasmid to tissue engineering scaffolds," Gene Therapy 17:1134-1141 (2010).
Schulz et al., "A Scalable System for Production of Functional Pancreatic Progenitors from Human Embryonic Stem Cells," PLoS One 7(5):1-17 (2012).
Seidlits et al., "Hydrogels for Lentiviral Gene Delivery," Expert Opinion on Drug Delivery 10(4):499-509 (2013).
Shepard et al., "Hydrogel Design for Supporting Neurite Outgrowth and Promoting Gene Delivery to Maximize Neurite Extension," Biotechnol Bioeng. 109(3):830-9 (2012).
Siletz et al., "Dynamic Transcription Factor Networks in Epithelial-Mesencymal Transition in Breast Cancer Models," Plos One. 8(4)1-20 (2013).
Sneddon et al., "Self-renewal of embryonic-stem-cell-derived progenitors by organ-matched mesenchyme," Nature 491:765-770 (2012).
Stacer et al., "NanoLuc Reporter for Dual Luciferase Imaging in Living Animals," Molecular Imaging 12(7):1-13 (2013).
Stoffel et al., "Localiation of Human Homeodomain Trascription Factor Insulin Promoter Factor 1(IPF1) to Chromosome Band 13q12.1," Genomics 28:125-126 (1995).
Sumpio et al., "Cells in focus: endothelial cell," Int J Biochem Cell Biol. 34(12):1508-1512 (2002).

(56) References Cited

OTHER PUBLICATIONS

Thomas et al., "Sponge-mediated Lentivirus Delivery to Acute and Chronic Spinal Cord Injuries," Journal of Controlled Release 204:1-10 (2015).

Vaithilingam et al., "Beneficial Effects of Coating Alginate Microcapsules with Macromolecular Heparin Conjugates—In Vitro and In Vivo Study," Tissue Eng Part A 20:324-334 (2014).

Villasenor et al., "Crosstalk between the developing pancreas and its blood vessels: an evolving dialogue," Semin Cell Dev Biol 23(6):685-692 (2012).

Weiss et al., "Dynamic transcription factor activity and networks during ErbB2 breast oncogenesis and targeted therapy," Integrative Biology 6:1170-1182 (2014).

Weizman et al., "The effect of endothelial cells on hESC-derived pancreatic progenitors in a 3D environment," Biomaterials Science 2:1706-1714 (2014).

Yamamoto et al., "A Novel Function of Onecut1 Protein as a Negative Regulator of MafA Gene Expression," Journal of Biological Chemistry 288:21648-21658 (2013).

Yap et al., "Collagen IV-Modified Scaffolds Improve Islet Survival and Functrion and Reduce Time to Euglycemia," Tissue Eng Part A 19(21 and 22):2361-2372 (2013).

Zhao et al., "The Islet β Cell-enriched MafA Activator Is a Key Regulator of Insulin Gene Transcription," Journal of Biological Chemistry 280(12):11887-1194 (2005).

Shepard et al., "Hydrogel Macroporosity and the Prolongation of Transgene Expression and the Enhancement of Angiogenesis," Biomaterials, 33:7412-21 (2012).

\* cited by examiner

A

B

MICROPOROUS HYDROGEL SCAFFOLDS FOR CELL TRANSPLANTATION

CROSS-REFERENCE TO RELATED APPLICATION

This application claims the priority benefit under 35 U.S.C. § 119(e) of Provisional U.S. Patent Application No. 62/442,768, filed Jan. 5, 2017, the disclosure of which is incorporated herein by reference in its entirety.

FIELD OF THE DISCLOSURE

The present disclosure relates generally to biomaterial implants and methods for delivering a cell to an individual in need thereof and, more particularly, to biomaterial implants and techniques for delivering an islet cell and/or a β-cell progenitor to an individual.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Clinical islet transplantation has the potential to become a cure for Type 1 Diabetes (T1D). However, a number of barriers limit the widespread application of this technology. A translatable supply of islets and the underlying autoimmune and immune response to the transplanted cells reflect two major barriers. A third major challenge is the isolation of a transplantable site for the long-term engraftment and functionality of islets. Clinically, islets are transplanted intrahepatically, which is associated with an instant blood mediated inflammatory response (IBMIR) that can damage the cells. Furthermore, the liver has numerous critical functions and thus little can be done to alter this transplantation site. Extrahepatic sites have been investigated, primarily using encapsulation approaches to protect islets from the host immune response. However, these approaches often lead to the exclusion of blood vessels that would normally revascularize the islets.

SUMMARY OF THE INVENTION

The present disclosure is generally directed to islet cell transplantation onto microporous scaffolds that allow for revascularization of the transplanted islets. The ability to revascularize the islets distinguishes this approach from encapsulation systems, as revascularization can provide the nutrients necessary for islet survival while also facilitating the sensing of blood glucose and the distribution of insulin. Islet encapsulation technologies using hydrogels for extrahepatic islet transplantation have become widespread in the cell transplantation field, due to their ability to shield encapsulated cells from the host's immune system. However, previous technologies are limited by preventing neovascularization and hindering mass transport of nutrients to encapsulated cells.

Therefore, and in some aspects, the present disclosure is directed to microporous PEG hydrogel scaffolds (non-encapsulating) for the transplantation of islets and/or β-cell progenitors to a clinically translatable, extrahepatic site (for example and without limitation, the omentum or the epididymal fat in mouse models).

In various embodiments of the present disclosure, these microporous scaffolds have been functionalized to control the local environment. In at least some embodiments, the microporous scaffolds are functionalized (e.g., with extracellular matrix proteins and/or trophic factors) to enhance the engraftment of the transplanted islets. Additionally or alternatively, in some embodiments, the microporous scaffolds are functionalized (e.g., with immune cytokines and/or Tregs) to modulate the innate and adaptive immune responses to delay rejection or promote immune tolerance. Accordingly, in various embodiments, the microporous scaffolds have been functionalized to increase success of cell transplantation.

In some aspects the disclosure provides a biomaterial implant comprising a microporous scaffold comprising poly(ethylene glycol) (PEG) or poly(lactide-co-glycolide) (PLG), wherein the scaffold comprises, or includes thereon, (i) an extracellular matrix (ECM) molecule and (ii) an islet cell and/or a β-cell progenitor. In various embodiments, the PEG is 4-arm PEG or 8-arm PEG. In further embodiments, the PEG is at least about 10, 15, 20, 25, 30, or more kilodaltons (kDa) molecular weight.

In some embodiments, the extracellular matrix molecule is collagen, laminin, or fibronectin. In further embodiments, a combination of extracellular matrix molecules is utilized. Thus, in some embodiments, a scaffold of the disclosure comprises collagen and laminin, collagen and fibronectin, and/or laminin and fibronectin. In further embodiments, the scaffold comprises collagen and laminin.

In various embodiments, a biomaterial implant of the disclosure further comprises an endothelial cell or mesenchyme. In further embodiments, a biomaterial implant of the disclosure further comprises vascular endothelial growth factor (VEGF). In still further embodiments, a biomaterial implant of the disclosure further comprises a trophic factor. In some embodiments, the trophic factor is exendin-4.

In some embodiments, the scaffold comprises about 500, 600, 700, 800, 900, 1000 or more islet equivalents per square centimeter ($cm^2$). In further embodiments, the scaffold comprises about 5 million, 10 million, 20 million, 30 million, 40 million, 50 million or more β-cell progenitors per square centimeter ($cm^2$). In related embodiments, the scaffold comprises both the islet cell and the β-cell progenitor.

In yet additional embodiments, a biomaterial implant of the disclosure is about 35 millimeters (mm) in diameter. In some embodiments, the average pore size in the scaffold is from about 250 to about 600 micrometers (μm). In some embodiments, the islet cell and/or the β-cell progenitor is not encapsulated within the scaffold.

In further aspects, the disclosure provides a method of treating Type 1 diabetes in a subject in need thereof, comprising implanting a biomaterial implant of the disclosure into the subject. In some embodiments, the implanting is subcutaneous. In further embodiments, the implanting occurs at one site in the subject. In still further embodiments, the implanting occurs at more than one site in the subject. In related embodiments, the site is the peritoneum, omentum, or muscle.

In some embodiments, one biomaterial implant is implanted.

In further embodiments, more than one biomaterial implant is implanted. In related embodiments, 5, 10, 15, 20 or more biomaterial implants are implanted.

In various embodiments, a method of the disclosure further comprises removing the biomaterial implant or implants.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

In FIG. 4, *P<0.01, **P<0.005.

DETAILED DESCRIPTION

Islet transplantation is a promising curative therapy for type 1 diabetes (T1D) [Barton et al., Improvement in outcomes of clinical islet transplantation: 1999-2010. Diabetes Care. 2012; 35: 1436-45], for which exogenous insulin therapy is frequently insufficient to prevent the debilitating acute and/or chronic complications. Clinically, islets are transplanted intrahepatically; however, a decade of research has identified that the local pro-inflammatory and pro-thrombotic milieu within the liver contribute significantly to poor islet engraftment at this site and compromise their long-term function [Ozmen et al., Diabetes. 2002; 51: 1779-84; Citro et al., Current diabetes reports. 2013; 13:733-44]. Intrahepatically transplanted islets have been found to be subjected to an "instant blood mediated inflammatory reaction (IBMIR)," which is an activation of the innate immune system that leads to the immediate release of tissue factor and inflammatory cytokines, and attraction of innate immune cells to the transplanted islets that can lead to graft failure [Moberg, Upsala journal of medical sciences. 2005; 110:17-55].

To overcome this immune system response, researchers have developed extrahepatic transplantation methods utilizing encapsulation systems. These encapsulation systems encapsulate the islets within a hydrogel, which does successfully shield the cells from the host's immune system but limits nutrient diffusion and angiogenesis. Without the ability to sufficiently vascularize, the cells' ability to sense glucose and release insulin in the bloodstream is limited and their long-term viability is harmed.

Microporous scaffolds have been developed, which also can be employed to support extrahepatic transplantation, and thereby avoid the IBMIR. Advantageously, such microporous scaffolds function to create and maintain a space for islet engraftment and vascularization, and support their long-term function [Blomeier et al., Transplantation. 2006; 82:452-9; Salvay et al., Transplantation. 2008; 85:1456-64]. The vascularization of the islets on microporous scaffolds can provide the nutrients necessary for islet survival while also facilitating the sensing of blood glucose and the distribution of insulin.

Figure 3:
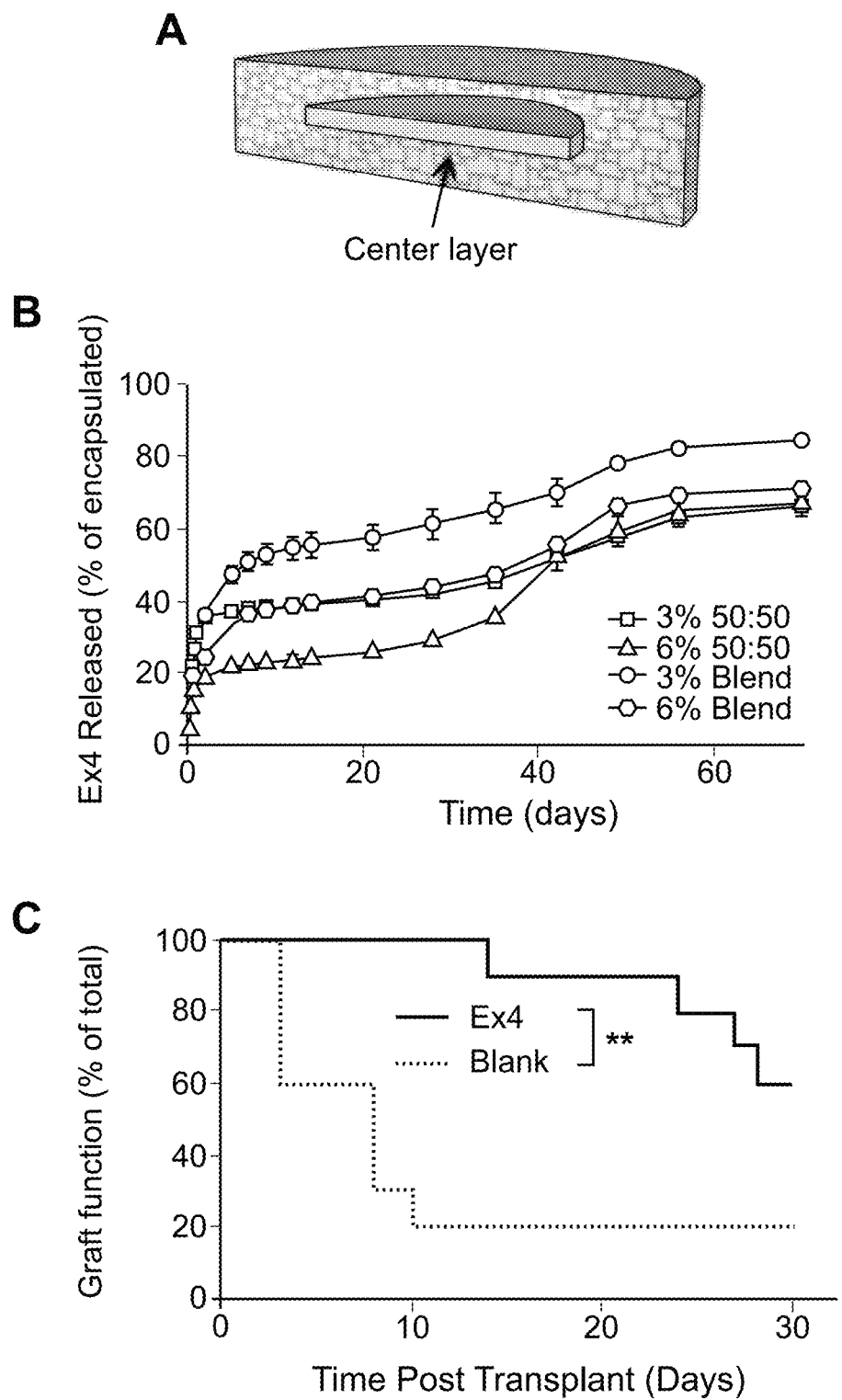
FIG. 3 shows that Ex4-releasing scaffolds support engraftment of human islets. Specifically, (A) depicts a cross-sectional schematic of a layered scaffold demonstrating the outer layer molded around a smaller solid inner layer that does not span the width of the scaffold. (B) depicts a graph of the Ex4 release rate from the scaffolds. (C) depicts a graph of graft function using 3% 50:50 Ex4 scaffolds compared to blank scaffolds (n=10, ** p<0.01).
Figure 4:
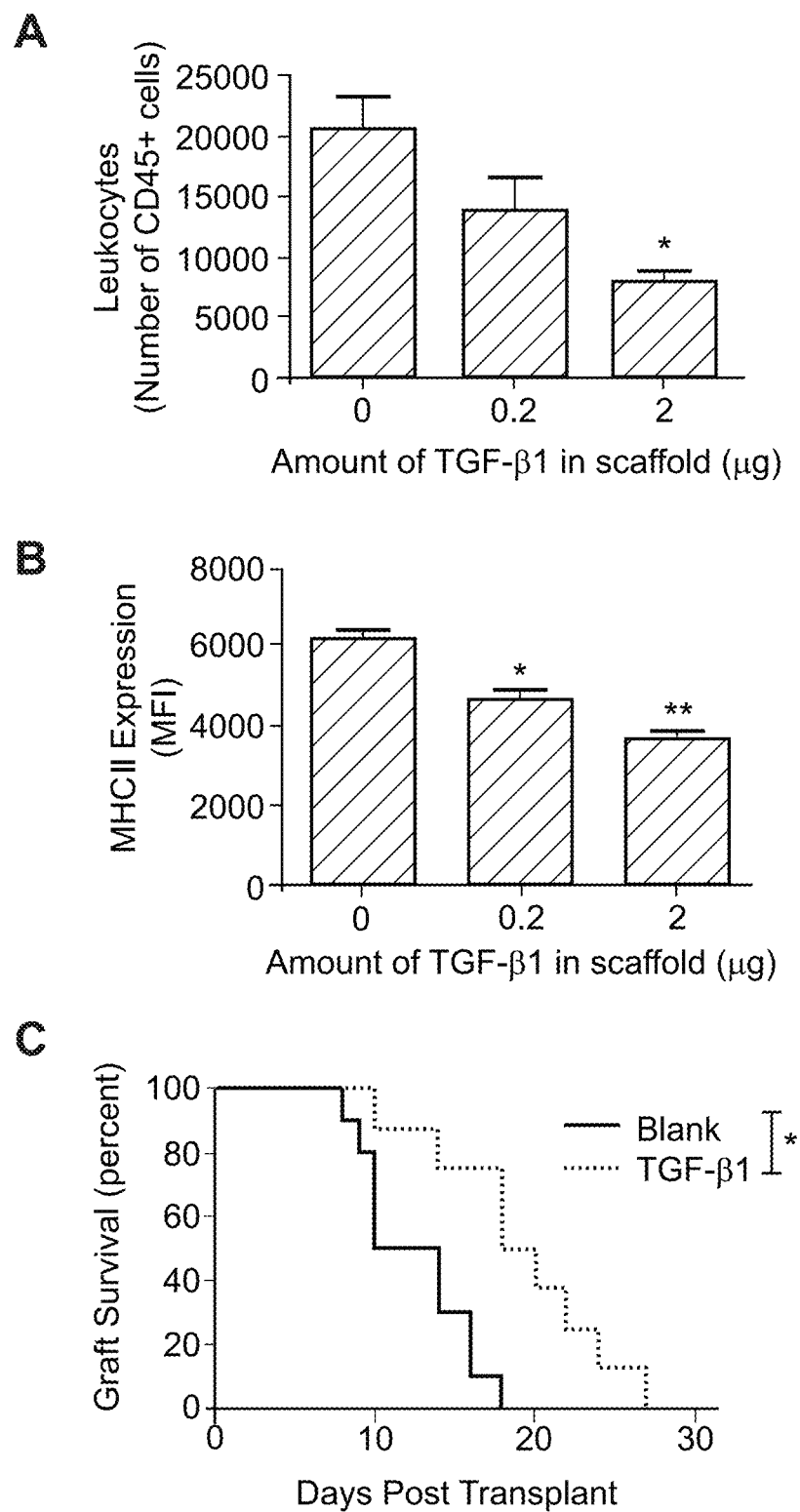
FIG. 4 shows that TGF-β-releasing scaffolds exhibit decreased inflammation. Specifically, (A) depicts a bar graph showing the number of scaffold-infiltrating $CD45^+$ cells 7 days after implant. (B) depicts a bar graph showing MHCII expression of scaffold-infiltrating CD11b+F4/80+ macrophages. (C) depicts a graph of islet allograft survival in the BALB/c→B6 transplant model.

Furthermore, microporous scaffolds have the potential to be functionalized to present factors that can promote survival and function. This ability to control the local environment post-transplantation is important for at least two reasons: i) the islet quality, despite strict release criteria, can vary between donors and ii) the microenvironment within the transplant site may vary between recipients, and the presentation of biological signals that provide a defined, permissive environment for the islets enhances the likelihood of a successful outcome for the transplant. Scaffolds have been developed that enhance islet engraftment and function through the presentation of ECM proteins (FIG. 1) [Salvay et al., Transplantation. 2008; 85:1456-64; Yap et al., Tissue Eng Part A. 2013; 19:2361-72], delivery of trophic factors (FIG. 3) [Hlavaty et al., American Journal of Transplantation. 2014; 14:1523-32], and through localized immunomodulation (FIG. 4) [Gower et al., Biomaterials. 2014; 35:202431; Liu et al., Biomaterials. 2016; 80:11-9; Graham et al., PLG Scaffold Delivered Antigen-Specific Regulatory T Cells Induce Systemic Tolerance in Autoimmune Diabetes. Tissue Engineering Part A. 2013; 19:1465-75]. Furthermore, these scaffolds have been effective with the induction of tolerance to the transplanted cells, which may result from an attenuated response of the innate immune system relative to that observed within the liver [Kheradmand et al., Biomaterials. 2011; 32:4517-24]. However, these past scaffolds have been formed of poly (lactide-co-glycolide) (PLG). Unfortunately, the development of a clinically viable PLG scaffold for islet transplantation has been hindered by the foreign body response the host has to PLG. As described further herein (see Example 8), in primates, transplantation of islets on PLG scaffolds was found to cause a fairly severe immune response that resulted in fibrosis and cell ingrowth.

Advantageously, the present disclosure is directed, in some aspects, to a scaffold formed of PEG. The PEG scaffolds of the present disclosure differ from the scaffolds discussed above at least in that the PEG material of the present disclosure is hydrophilic and will adsorb proteins and have a distinct foreign body response. Additionally, the PEG hydrogels of the present disclosure are either non-degradable or degrade by mechanisms that are different from PLG. The mechanics of the hydrogels are also different from that of the PLG scaffolds, which can influence a number of cellular responses. Advantageously, as exemplified herein (see Example 8), PEG hydrogels have a milder foreign body/immune response in vivo when compared with PLG scaffolds. In some embodiments, the scaffolds are functionalized to further reduce the immune response.

Accordingly, in some aspects the present disclosure provides biomaterial implant comprising a microporous scaffold comprising poly(ethylene glycol) (PEG) or poly(lactide-co-glycolide) (PLG). In some aspects of the disclosure, the scaffold includes (i) an extracellular matrix (ECM) molecule and (ii) an islet cell and/or a β-cell progenitor attached thereto.

In some embodiments, the biomaterial implant further comprises vascular endothelial growth factor (VEGF).

In some embodiments, the scaffold is porous and/or permeable. In some embodiments, the scaffold provides an environment for attachment, incorporation, adhesion, encapsulation, etc. of agents (e.g., DNA, protein, cells, etc.). In some embodiments, agents are released (e.g., controlled or sustained release) to enhance islet survival and function post-transplantation through decreased apoptosis, increased glucose stimulated insulin secretion, and increased metabolic activity. With regard to agents (e.g., therapeutic agents) and sustained release, for long term therapy (e.g., days, weeks or months) and/or to maintain the highest possible drug concentration at a particular location in the body, the present disclosure in certain embodiments provides a sustained release depot formulation with the following non-limiting characteristics: (1) the process used to prepare the matrix does not chemically or physically damage the agent; (2) the matrix maintains the stability of the agent against denaturation or other metabolic conversion by protection until release, which is important for very long sustained release; (3) the entrapped agent is released from the hydrogel composition at a substantially uniform rate, following a kinetic profile, and furthermore, a particular agent can be prepared with two or more kinetic profiles, for example, to provide in certain embodiments, a loading dose and then a sustained release dose; (4) the desired release profile can be selected by varying the components and the process by which the matrix is prepared; and (5) the matrix is nontoxic and degradable. Accordingly, in some embodiments an agent is configured for specific release rates. In further embodiments, multiple different agents are configured for different release rates. For example, a first agent may release over a period of hours while a second agent releases over a longer period of time (e.g., days, weeks, months, etc.). In some embodiments, and as described above, the scaffold or a portion thereof is configured for sustained release of agents. In some embodiments, the sustained release provides release of biologically active amounts of the agent over a period of at least 30 days (e.g., 40 days, 50 days, 60 days, 70 days, 80 days, 90 days, 100 days, 180 days, etc.).

Porosity. In some embodiments, the scaffold or a portion thereof is configured to be sufficiently porous. As demonstrated herein (see Example 6), large pore PEG scaffolds facilitate the most efficient differentiation of cells to pancreatic endoderm cells. Thus, the size of the pores in a scaffold of the disclosure (e.g., a PEG scaffold or a PLG scaffold) may be selected for particular cell types of interest and/or for the amount of ingrowth desired and are, for example without limitation, at least about 20 µm, 30 µm, 40 µm, 50 µm, 100 µm, 200 µm, 500 µm, 700 µm, or 1000 µm. In some embodiments, the pore size is from about 425 to about 600 µm, or from about 500 to about 600 µm, or from about 550 µm to about 600 µm. In further embodiments, the pore size is at least about 425 µm, or at least about 500 µm. In some embodiments, the pore size is from about 250-425 µm. In some embodiments, the PEG gel is not porous but is instead characterized by a mesh size that is, e.g., 10 nanometers (nm), 15 nm, 20 nm, 25 nm, 30 nm, 40 nm, or 50 nm.

In some aspects, the disclosure is directed to transplantation of islet cells and/or beta-cell progenitors to a patient in need thereof (e.g., a patient suffering from Type 1 diabetes) comprising implanting a biomaterial implant of the disclosure in the patient. The biomaterial implant comprises, in various embodiments, a PEG scaffold or a PLG scaffold with an ECM molecule and the islet cells and/or beta-cell progenitors attached thereto and, optionally, therein. In some embodiments in which islet cells are transplanted, the implant comprises a scaffold (e.g., a PEG or PLG scaffold) having a pore size of from about 250 to about 425 micrometers (µm). In some embodiments in which beta-cell progenitors are transplanted, the implant comprises a scaffold (e.g., a PEG or PLG scaffold) having a pore size of from about 425 to about 600 µm. In some embodiments in which both islet cells and beta-cell progenitors are transplanted, the implant comprises a scaffold (e.g., a PEG or PLG scaffold) having a pore size of from about 250 to about 600 micrometers (µm); in other embodiments with both islet cells and beta-cell progenitors transplanted, the implant comprises a scaffold (e.g., a PEG or PLG scaffold) having a pore size of from about 425 to about 600 micrometers (µm).

We now describe an example fabrication, characterization, and implantation of microporous scaffolds in accordance with examples herein.

In some aspects, the scaffolds are formed of a substantially non-degradable polymer, e.g., polyethylene glycol (PEG). Degradable hydrogels encapsulating gelatin microspheres may be formed based on a previously described Michael-Type addition PEG hydrogel system with modifications [Shepard et al., Biotechnol Bioeng. 109(3): 830-9 (2012)]. Briefly, four-arm poly(ethylene glycol) vinyl sulfone (PEG-VS) (20 kDa) is dissolved in 0.3 M triethanolamine (TEA) pH 8.0 at a concentration of 0.5 mg/µL to yield a final PEG concentration of 10%. In some embodiments, and as disclosed herein, eight-arm PEG is utilized. The plasmin-degradable trifunctional (3 cysteine groups) peptide crosslinker (Ac-GCYKNRCGYKNRCG) is dissolved in 0.3 M TEA pH 10.0 to maintain reduction of the free thiols at a concentration that maintain a stoichiometrically balanced molar ratio of VS:SH. Prior to gelation, gelatin microspheres are hydrated with 10 µL sterile Millipore or lentivirus solution. Subsequently, the PEG and peptide crosslinking solutions are mixed well and immediately added to the hydrated gelatin microspheres for encapsulation. In some embodiments, and as described above, salt is used as the porogen instead of gelatin microspheres. In this case, the PEG solution is made in a saturated salt solution, so that the porogen does not significantly dissolve.

In some embodiments, and as discussed in the Examples herein, UV crosslinking is used instead of peptide crosslinking. Ultraviolet crosslinking is contemplated for use with PEG-maleimide, PEG-VS, and PEG-acrylate.

PLG scaffolds and methods of their production are generally described in Jang et al., [J Control Release. 2006 112(1):120-8], Jange et al., [J Biomed Mater Res A. 2006 77(1):50-8], and Rives et al. [Biomaterials. 2009 30(3):394-401] which are each incorporated by reference herein in their entirety.

In various embodiments, a scaffold of the disclosure further comprises an endothelial cell or mesenchyme. Endothelial cells form the inner lining of a blood vessel and provide an anticoagulant barrier between the vessel wall and blood. The endothelial cell reacts with physical, chemical, and biological properties of the material and stimuli within the circulation to regulate hemostasis, vasomotor tone, and immune and inflammatory responses. In addition, the endothelial cell is pivotal in angiogenesis and vasculogenesis [Sumpio et al., Int J Biochem Cell Biol. 2002; 34(12): 1508-12]. "Mesenchyme" comprises mesenchymal cells, which are cells of mesodermal origin that are capable of developing into connective tissues, blood, and lymphatic and blood vessels.

Methods and Administration

In some aspects, the present disclosure provides biomaterial implants comprising scaffolds and methods of their use in treating Type I diabetes in a subject. The scaffolds, in some embodiments, are PEG scaffolds. In various embodiments, the scaffolds have (i) an extracellular matrix molecule and (ii) an islet cell and/or a β-cell progenitor. In some embodiments, the scaffold includes both the islet cell and the β-cell progenitor attached thereto. By way of non-limiting example, a PEG scaffold is formed from a PEG polymer solution, which is mixed with salt or other porogen and a curing agent. It is placed in a mold and polymerized with UV light to achieve cross-linking and form the hydrogel. The structure is then placed in water to dissolve the porogen, which creates pores in the scaffold. Protein solutions and cell suspensions are then added to the scaffold (for example, by pipetting them onto the scaffold). The cells adhere to the proteins on the outside of the scaffold and are lodged into depressions within the scaffold. Thus, the cells are physically and chemically seeded onto the scaffold, resulting in long-term cell attachment.

In various embodiments, the scaffold is about 35 millimeters (mm) in diameter. In further embodiments, the scaffold is about or is at least about 10, 20, 25, 30, 35, 40, 45, or 50 mm in diameter. In still further embodiments, the scaffold is from about 10 to about 50, 20 to about 40, 10 to about 30, 10 to about 20, 20 to about 50, or from about 20 to about 40, or from about 20 to about 35, or from about 20 to about 30 mm in diameter. In related embodiments, the scaffold is from about 30 to about 50 or from about 30 to about 40 mm in diameter.

In some embodiments, the scaffold comprises about or at least about 500, 600, 700, 800, 900, 1000 or more islet equivalents per square centimeter (cm$^2$). In further embodiments, the scaffold comprises from about 500 to about 1000 islet equivalents per cm$^2$, or from about 500 to about 900 islet equivalents per cm$^2$, or from about 500 to about 800 islet equivalents per cm$^2$, or from about 500 to about 700 islet equivalents per cm$^2$, or from about 500 to about 600 islet equivalents per cm$^2$, or from about 700 to about 1000 islet equivalents per cm$^2$, or from about 800 to about 1000 islet equivalents per cm$^2$, or from about 900 to about 1000 islet equivalents per cm$^2$.

In certain embodiments, the scaffold comprises about or at least about 5 million, 10 million, 15 million, 20 million, 25 million, 30 million, 35 million, 40 million, 45 million, 50 million or more β-cell progenitors per square centimeter (cm$^2$). In further embodiments, the scaffold comprises from about 5 million to about 50 million β-cell progenitors per cm$^2$, or from about 5 million to about 40 million β-cell progenitors per cm$^2$, or from about 5 million to about 30 million β-cell progenitors per cm$^2$, or from about 5 million to about 20 million β-cell progenitors per cm$^2$, or from about 5 million to about 10 million β-cell progenitors per cm$^2$, or from about 10 million to about 50 million β-cell progenitors per cm$^2$, or from about 10 million to about 40 million β-cell progenitors per cm$^2$, or from about 10 million to about 30 million β-cell progenitors per cm$^2$, or from about 10 million to about 20 million β-cell progenitors per cm$^2$.

In some embodiments, the biomaterial implant is implanted subcutaneously. In further embodiments, the implanting occurs at one site in the subject, while in other embodiments the implanting occurs at more than one site in the subject. In various embodiments, the site is the peritoneum, omentum, or muscle.

In related embodiments, one biomaterial implant is implanted. In further embodiments, more than one biomaterial implant is implanted. In still further embodiments, 5, 10, 15, 20 or more biomaterial implants are implanted. In further examples, at least 1, at least 2, at least 3, at least 4, at least 5, at least 6, at least 7, at least 8, at least 9, at least 10, from about 5 to about 10, or from about 5 to about 15, or from about 10 to about 15, or from about 10 to about 20 scaffolds are implanted in a subject.

The present disclosure also contemplates that, in some embodiments, the biomaterial implant or implants is/are removed from the subject.

The disclosure also contemplates a scaffold which comprises a therapeutic agent. "Therapeutic agent" as used herein means any compound useful for therapeutic purposes. The term as used herein is understood to mean any compound that is administered to a subject for the treatment of a condition. Thus, in some embodiments one or more agents are associated with a scaffold to provide a therapeutic benefit to a subject. Agents may be associated with the scaffold by covalent or non-covalent interactions, adhesion, encapsulation, etc. In some embodiments, a scaffold comprises one or more agents adhered to, adsorbed on, encapsulated within, and/or contained throughout the scaffold. The present disclosure is not limited by the nature of the agents. Such agents include, but are not limited to, proteins, nucleic acid molecules, small molecule drugs, lipids, carbohydrates, cells, cell components, and the like. In various embodiments, the agent is a therapeutic agent. In some embodiments, two or more (e.g., 3, 4, 5, 6, 7, 8, 9, 10 . . . 20 . . . 30 . . . 40 . . . , 50, amounts therein, or more) different agents are included on or within the scaffold. In some embodiments, agents associated with a scaffold include metastatic markers, such as: CD133 (which generally defines all progenitors), VEGFR-1 (hematopoietic progenitor cells (HPCs)), VEGFR-2 (endothelial progenitor cells (EPCs)), CD11b and GR1 (myeloid-derived suppressor cells), F4/80 and CD11b (macrophages), and CD11b+CD115+Ly6c+(inflammatory monocytes).

The present disclosure is applicable to any hydrophobic drug or other therapeutic agent for which delivery is desired. Non-limiting examples of such agents are found in U.S. Pat.

No. 7,611,728, which is incorporated by reference herein in its entirety. Additional therapeutic agents contemplated for use are found in PCT/US2010/55018, which is incorporated by reference herein in its entirety.

Scaffolds and methods disclosed herein, in various embodiments, are provided wherein the scaffold comprises a multiplicity of therapeutic agents. In some aspects, compositions and methods are provided wherein the multiplicity of therapeutic agents are specifically associated with one scaffold. In other aspects, the multiplicity of therapeutic agents are associated with more than one scaffold.

Definitions

The term "scaffold," as used herein, refers to a means of physical support for use in tissue engineering or tissue regeneration. Scaffolds of the present disclosure may comprise any of a large variety of structures including, but not limited to, particles, beads, polymers, surfaces, implants, matrices, etc. Scaffolds may be of any suitable shape, for example, spherical, generally spherical (e.g., all dimensions within 25% of spherical), ellipsoidal, rod-shaped, globular, polyhedral, etc. The scaffold may also be of an irregular or branched shape.

"PEG" refers to polyethylene glycol. "Average molecular weight" is given its ordinary and accustomed meaning of the arithmetic mean of the molecular weights of the components (e.g., molecules) of a composition, regardless of the accuracy of the determination of that mean. For example, polyethylene glycol, or PEG, having an average molecular weight of 3.5 kilodaltons may contain PEG molecules of varying molecular weight, provided that the arithmetic mean of those molecular weights is determined to be 3.5 kilodaltons at some level of accuracy, which may reflect an estimate of the arithmetic mean, as would be understood in the art. Any PEG is contemplated for use in the compositions and methods of the disclosure. In general, the PEG has an average molecular weight of at least about 5,000 daltons. In further embodiments, the PEG has an average molecular weight of at least or at least about 10,000 daltons, 15,000 daltons, 20,000 daltons, 25,000 daltons, 30,000 daltons, and is preferably between 10,000 and 30,000 daltons, or between 15,000 and 20,000 daltons. Also preferred is PEG having an average molecular weight of 5,000, of 6,000, of 7,000, of 8,000, of 9,000, of 10,000, of 11,000, of 12,000 of 13,000, of 14,000, 15,000, 20,000, 25,000, or of 30,000 daltons or more. In various embodiments, the PEG is a four-arm PEG or an eight-arm PEG.

"PLG" refers to poly(D,L-lactide-co-glycolide). "PLGA" refers to a copolymer of D,L-lactide and glycolide. Poly(d,l-lactide-co-glycolide) (PLG) with 75:25 mole ratio of lactide to glycolide was obtained from Boehringer Ingelheim Chemical (Resomer 755, i.v.=0.6-0.8, 80-120 kDa; Resomer 752, i.v.=0.116-0.24, 11-24 kDa, Petersburg, Va.). Resomer 755 and Resomer 752 are referred to as "high molecular weight" (HMW) and "low molecular weight" (LMW), respectively.

An extracellular matrix "ECM" molecule refers, for example and without limitation, to collagen, laminin, and/or fibronectin.

The term "about" means within 20%, preferably within 10%, and more preferably within 5%.

In some embodiments, a scaffold of the disclosure further comprises a trophic factor. "Trophic factors" are factors desirable for growth and survival of various classes of cells in tissues. Trophic factors are generally macromolecular proteins. In various embodiments, the trophic factor is exendin-4.

As used in this specification and the appended claims, the singular forms "a", "an", and "the" include plural references unless the context clearly dictates otherwise.

All publications mentioned herein are incorporated herein by reference in their entirety.

EXAMPLES

The non-limiting examples contemplated herein are directed to advancing the biomaterial implants of the disclosure to the clinic by i) translating islet transplantation on microporous scaffolds to non-human primate models, then to early clinical trials, and ii) investigating the transplantation of hESC-derived β-cell progenitors. Advantages of the microporous scaffolds disclosed herein include that, in some embodiments, they are formed from PEG, which is a material that has been FDA approved and is used widely for a number of applications; thus there is a low barrier to translation.

These scaffolds can be easily manufactured under GMP conditions at a reasonable cost and effectively stored for long times. The method for gelation formation creates non-degradable scaffolds, which allows for the graft to be retrieved should the need arise, such as excessive inflammation, infection, or teratoma formation associated with the hESC-derived cells. While microporous scaffolds have demonstrated efficacy with human islets [Gibly et al., Biomaterials. 2011; 32:9677-84; Hlavaty et al., American Journal of Transplantation. 2014; 14:1523-32], these studies will investigate the scale-up and transplantation in large animal models and ultimately to patients. For the β-cell progenitors, these studies will investigate the scaffold design to support the cells at a clinically relevant extrahepatic site, and will also assess the safety of delivering these cells in a non-encapsulating system.

Example 1

Microporous Scaffolds Support Engraftment of Mouse and Human Islets

Microporous scaffolds for transplantation of islets into epididymal fat pads have been developed, which are clinically equivalent to the omentum [Blomeier et al., Transplantation. 2006; 82:452-9.]. Mouse islets seeded onto the microporous scaffolds quickly distributed within the scaffold pores, with 1-2 islets per pore (FIG. 1A). Fourteen days after implantation into a syngeneic host, islets were seen to maintain their morphology, demonstrate a dense and functional vasculature (staining for tomato lectin) (FIG. 1B), and additionally contain proliferating cells as indicated by PCNA staining, suggesting that turnover and remodeling were occurring within the islets (data not shown) [Gibly et al., Biomaterials. 2011; 32:9677-84]. The engrafted islets reversed host diabetes for 300 days (FIG. 1C), and hyperglycemia returned after explant of the fat pad (FIG. 1C). Interestingly, the scaffold lost integrity around 100 days and was not present at 300 d, and thus the islets remained functional throughout the time that the scaffold degraded [Salvay et al., Transplantation. 2008; 85:1456-64]. The ability to engineer the scaffold environment to enhance islet engraftment was initially demonstrated by modification of the scaffold with extracellular matrix (ECM) proteins collagen IV, which is shown to induce rapid euglycemia in diabetic hosts in a marginal mass islet transplant model (75 islets per recipient) (FIG. 1D).

Figure 2:
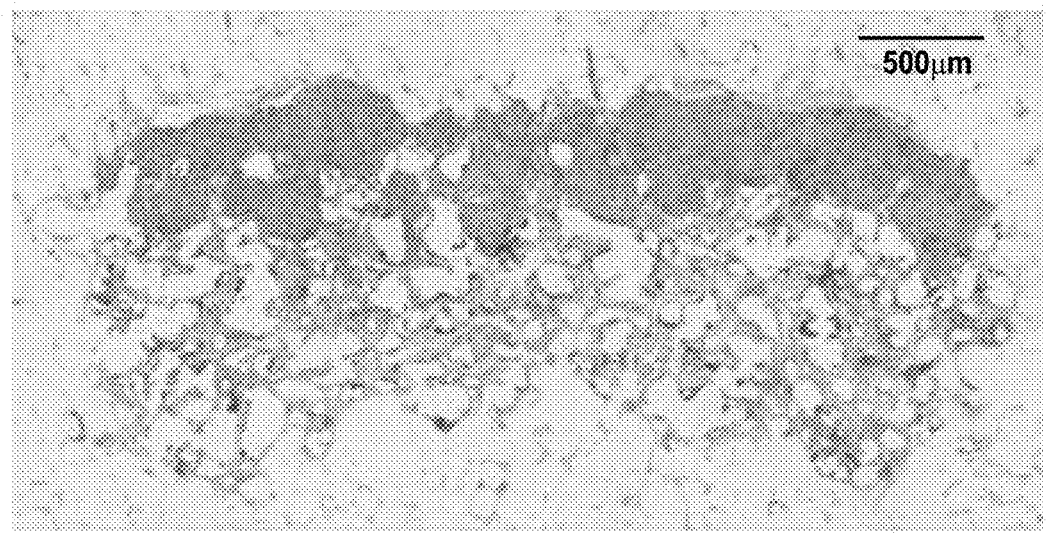
FIG. 2 shows long-term function of human islets transplanted on microporous scaffold. Specifically, (A) depicts trichrome stain of transplanted human islets 145 days post-transplant in NOD-SCID mouse. (B) depicts a graph of non-fasting blood glucose of human islets transplanted in either kidney capsules or on microporous scaffolds implanted in epididymal fat pads.
Figure 2:
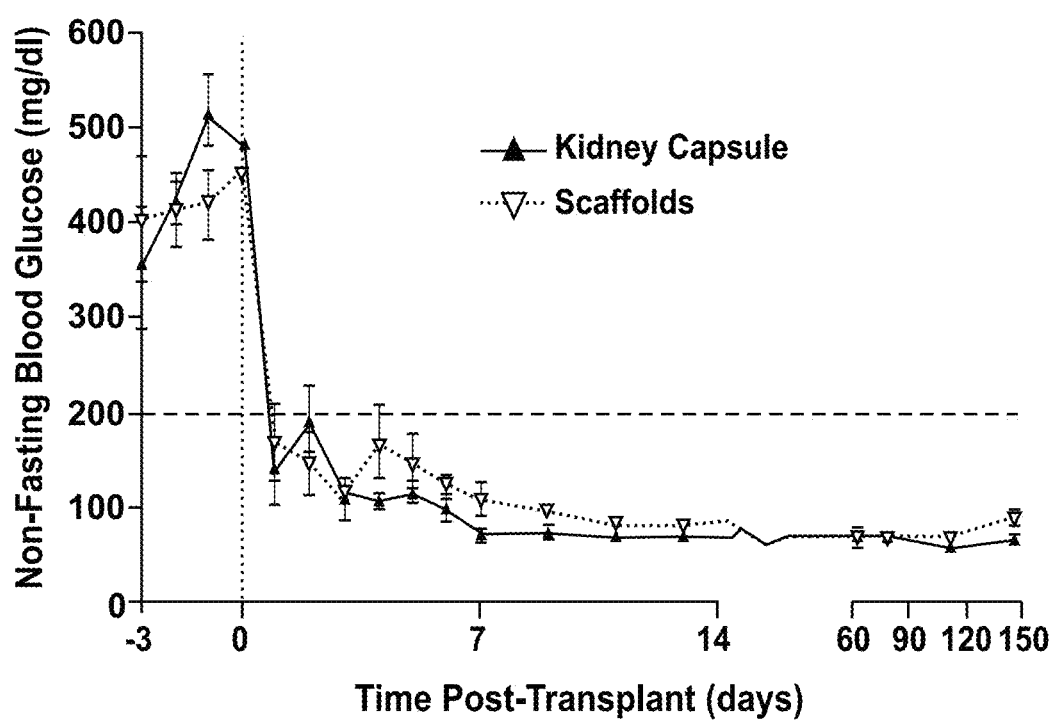

It was next investigated if microporous scaffolds could support engraftment of human islets which are distinct from murine islets in their cytoarchitecture, physiology, and glucose sensitivity. A substantially larger mass of human islet is needed, and it is disclosed herein that transplantation of 2000 islet equivalents (IEQ) consistently results in glycemic control for diabetic mice [Gibly et al., Cell transplantation. 2013; 22:811-9], a number that has been reported by others. This mass of islets can be delivered on two scaffolds with a diameter of 5 mm that fits the peritoneal fat pad of the mouse, and corresponds to a density of approximate 5000 IEQ/cm2. This density of islets has also been shown to have excellent survival following transplantation into the porcine omentum (FIG. 2) [Gibly et al., Biomaterials. 2011; 32:9677-84]. The reproducible restoration of normal blood glucose levels by transplantation of the cells at this density formed the basis for the studies in the non-human primate described elsewhere herein.

Protein-Releasing Scaffolds Support Engraftment of Human Islets

To further promote engraftment and reduce the required number of islets for establishing euglycemia, the scaffolds were modified to enable localized delivery of exendin-4 (Ex4), a glucagon-like protein-1 (GLP-1) receptor agonist that promotes β-cell survival and function[Park et al., The Journal of biological chemistry. 2006; 281:1159-68; Jhala et al., Genes & development. 2003; 17:1575-80]. Layered scaffolds were formed (FIGS. 3A and 3B) such that the outer layers were highly porous for cell transplantation, and the central core was composed of polymer microspheres loaded with Ex4 [Hlavaty et al., Am J Transplant. 2014 14(7):1523-32]. In vitro, Ex4 exhibited a bimodal release curve from the scaffold, with a strong initial release period of 7-10 days and a second, slower release occurring from days 15-70 (FIG. 3A). Both polymer composition (50:50 vs. 75:25 poly (lactic-co-glycolide)) and concentration (3% vs. 6%) during microsphere formation influenced the rate of initial and long-term Ex4 release (FIG. 3A). Human islets transplanted on Ex4-releasing scaffolds into diabetic NSG mice (mice lacking T, B and NK cells, therefore accept human islet grafts indefinitely) demonstrated more rapid restoration and longer-lasting of euglycemia compared to empty scaffolds (FIG. 3B). Importantly, the number of islets needed to achieve euglycemia ranged from 1500-1700 IEQ, significantly lower than the previous minimum of 2000 IEQ.

Microporous Scaffolds can Locally Modulate Immune Responses

Figure 5:
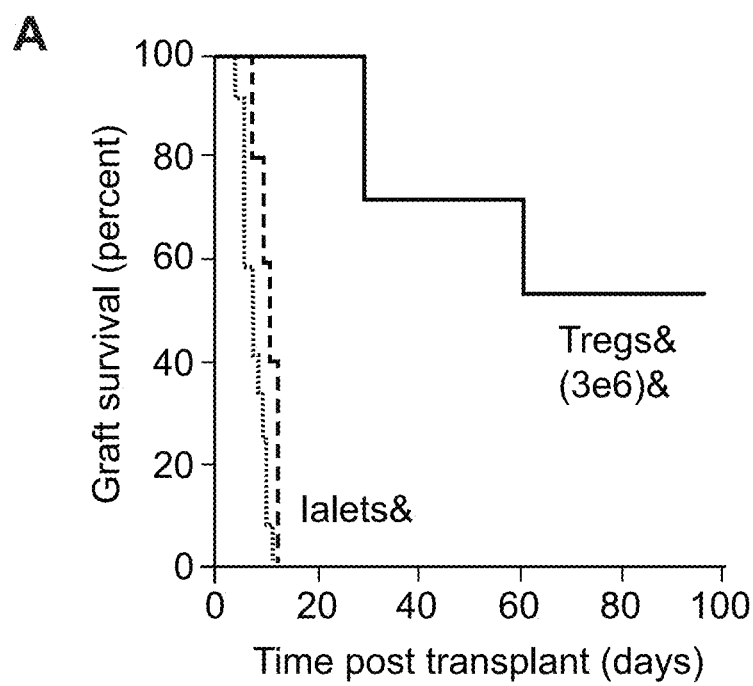
FIG. 5 depicts Treg-islet co-transplantation on scaffolds. Specifically, (A) depicts a graph showing graft survival over time for islet grafts transplanted with and without Treg. Co-transplantation of Tregs with islets enhances graft survival. (B) depicts immunofluorescent staining of a graft, showing that the scaffold microenvironment is conducive for Treg accumulation.
Figure 5:
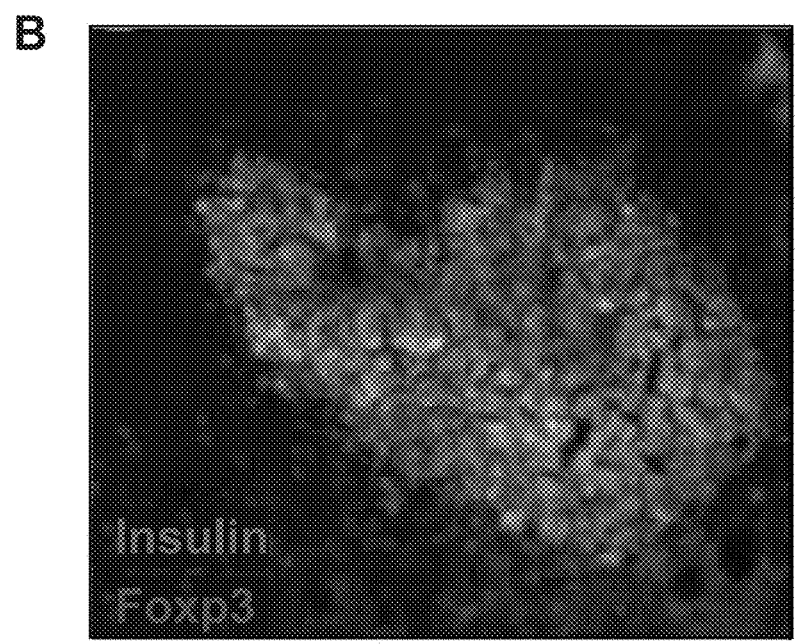
Figure 6:
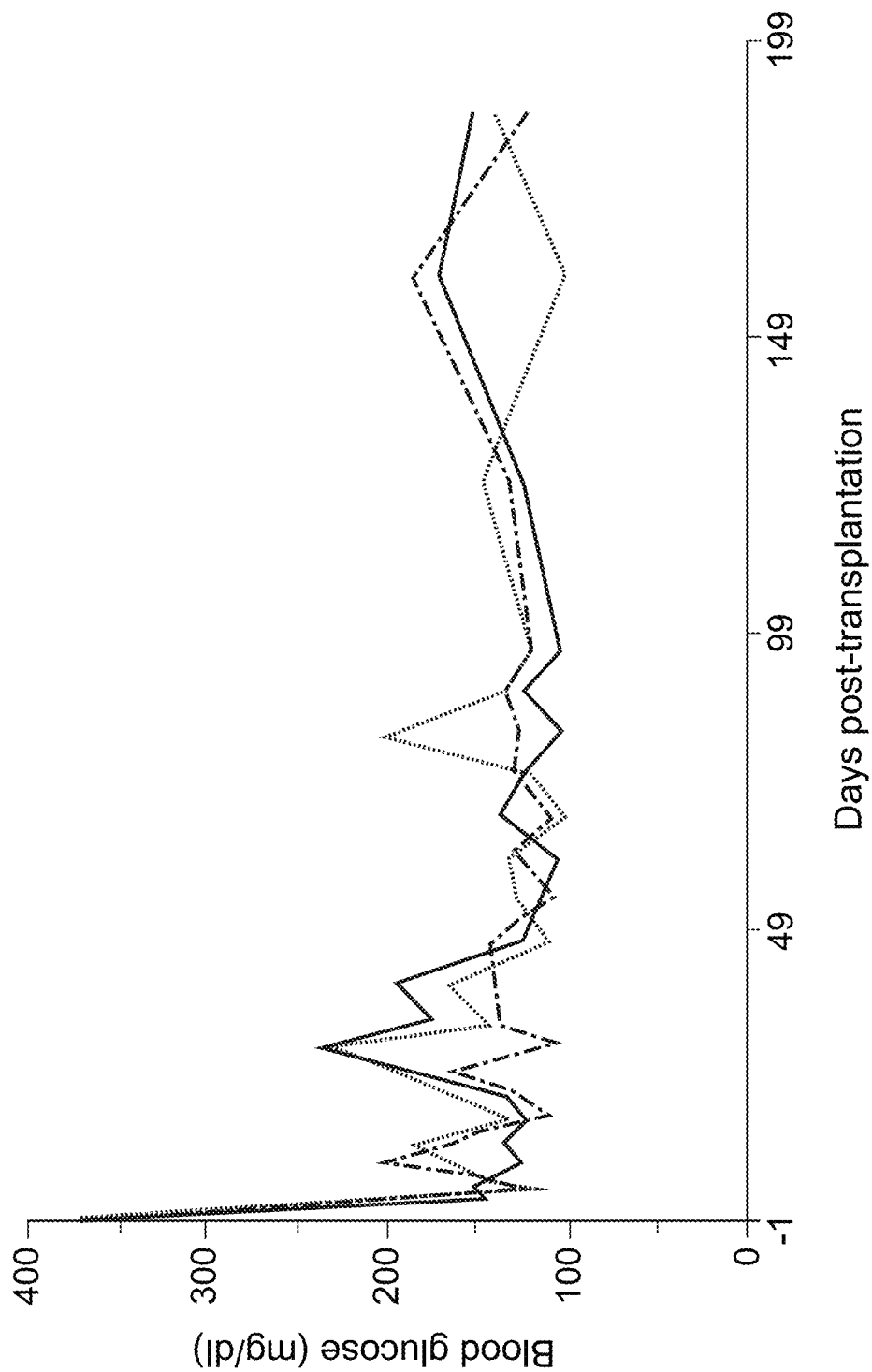
FIG. 6 depicts a graph of blood glucose measurements by day. The blood glucose measurements remained low/controlled following transplantation, demonstrating the survival of allogeneic islets in scaffolds. In the study, BALB/c islets (500/transplant) were transplanted on PLG scaffolds into epididymal fat pad of diabetic C57BL/6 mice. Animals were treated with 0.2 mg/kg *Rapa* starting the day of transplantation for 15 doses.

We used the same layered scaffolds described above (FIG. 3) [Hlavaty et al., Am J Transplant. 2014 14(7):1523-32] to deliver anti-inflammatory cytokine and chemokine to further modulate the scaffold micro-environment. Preliminary studies were performed to deliver TGF-β from the central layer of the scaffolds, and used such scaffolds for allogeneic islet cell transplant in mice. TGF-β-releasing scaffolds had fewer scaffold infiltrating CD45+ immune cells at day 7 (FIG. 4A), and the infiltrating CD11b+F4/80+ macrophages expressed a lower level of MHC II suggesting a less inflammatory phenotype (FIG. 4B). Additionally, scaffold release of TGF-β alone resulted in delayed graft rejection in a BALB/c→B6 allogeneic islet transplant model (FIG. 4C). This is highly encouraging in light of previously published data [Graham et al., Tissue engineering Part A. 2013; 19:1465-75] showing that loading of ex vivo expanded antigen-specific Tregs onto the scaffolds provided significant survival advantage for the transplant islet grafts in an autoimmune diabetes model (NOD→NOD transplant) (FIG. 5A). Collectively, these data suggest that microporous scaffolds can be engineered to attract more Tregs and its microenvironment is also compatible for their accumulation (FIG. 5B). Modification of islets or scaffolds with Fas-ligand (FasL) was also performed, which demonstrated the capacity to provide long-term protection of transplanted allogeneic islets (FIG. 6).

Figure 7:
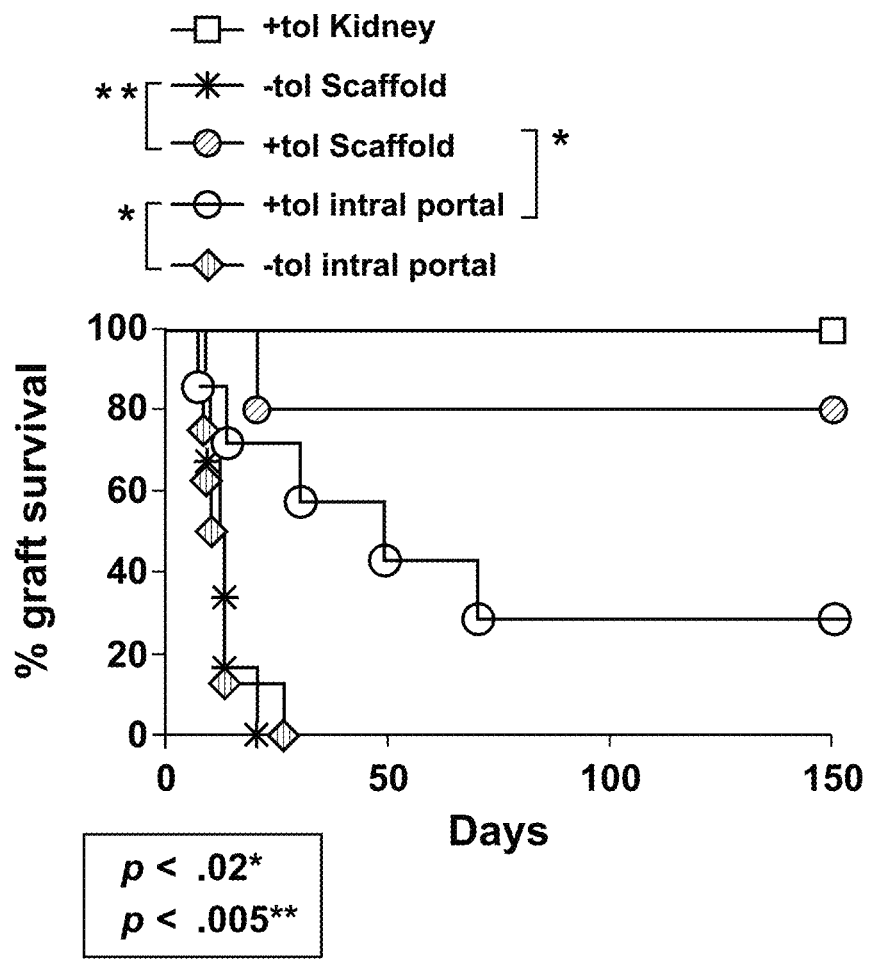
FIG. 7 depicts a graph of graft survival by day and compares the tolerance induction by donor ECDI-SP for scaffold- vs. intra-portally transplanted islets.

Microporous Scaffold-Delivered Islets are More Susceptible to Tolerance than Intra-Portally Transplanted Islets Immune tolerance through ECDI treated splenocytes has emerged as a promising strategy for the induction of immune tolerance, and scaffolds allow for tolerance induction more efficiently relative to transplantation of islets into the liver. Diabetic B6 recipients were treated on day −7 and day +1 with $10^8$ BALB/c ECDI-SP, and transplanted with BALB/c islets on day 0 either via microporous scaffolds or intra-portal infusion. As shown in FIG. 7, 80% of the islet allografts transplanted on scaffolds were permanently protected, similar to that observed with kidney capsule (KC) transplants (P=0.4, FIG. 7) [Kheradmand et al., Biomaterials. 2011; 32:4517-24]. In contrast, intra-portally transplanted islet allografts had significantly lower rate of graft protection (~30% long-term survival) compared with scaffold delivered islets (P=0.01, FIG. 7). Of note, the KC is the most widely used site for islet transplantation in mouse models but is not considered translational. These data suggest that site of islet transplantation may influence tolerance efficacy, possibly through modulation of local inflammation associated with the initial islet implantation.

Example 2

In some aspects, the present disclosure is directed toward the use of poly(ethylene glycol) (PEG) microporous scaffolds as a safe, efficient, and clinically applicable approach for transplantation of islets or hESC-derived n-cell progenitors. Questions examined in the examples relate to the scaffold design needed to create a supportive environment that maximally promotes engraftment and function of transplanted islets, or maturation of hESC-derived n-cell progenitors and subsequent normalization of blood glucose levels. Furthermore, the scaffolds are non-degradable which allows the implant to be explanted should the need arise; accordingly, these studies also assessed the efficacy of explantation at recovering transplanted cells.

Figure 1:
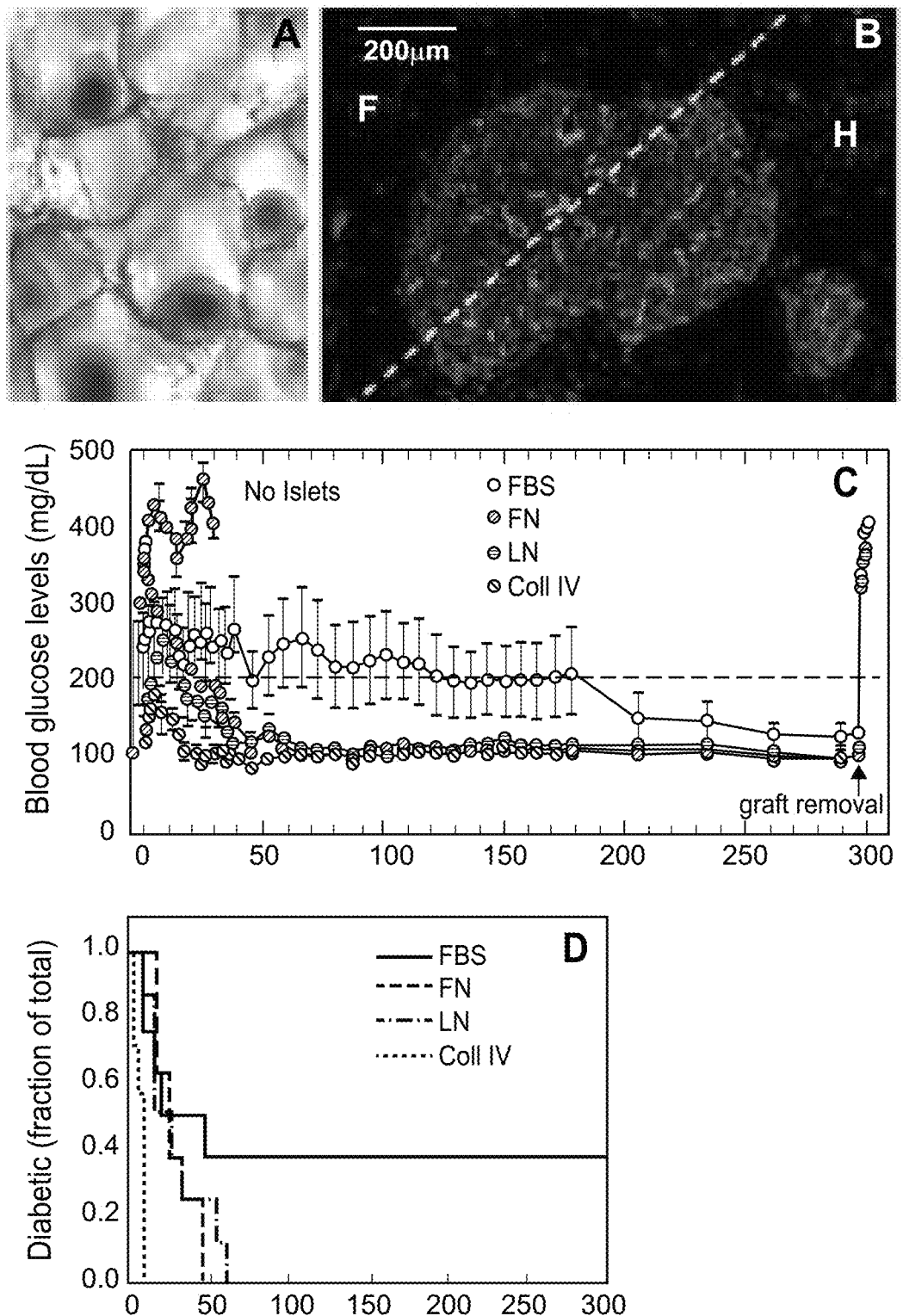
FIG. 1 shows that microporous scaffolds support engraftment of mouse islets. Specifically, (A) depicts a partial microscopic view of a scaffold seeded with islets. After islet seeding, scaffolds with 250-425 µm pores had islets individually or occasionally in pairs within pores. (B) depicts immunofluorescent staining for vasculature of scaffold transplanted islets. In the stained image, Red=insulin, Green=tomato lectin, Blue=nuclei. (C) depicts a graph of long term function of transplanted islets (125) on scaffolds in peritoneal fat pads. The arrow indicates the time of graft removal. (D) depicts a Kaplan Meier analysis of diabetes reversal for the ECM coatings, wherein: FBS=fetal bovine serum; FN=fibronectin; LN=laminin; Coll IV=collagen IV.

Research over the past 10 years with microporous scaffolds has demonstrated that transplanted islets engraft, become revascularized, and function to maintain normal blood glucose levels for long times (FIG. 1C). These scaffolds have supported the engraftment and function of human and porcine islets upon transplantation into mice [Gibly et al., Biomaterials 2011; 32:9677-84; Gibly et al., Cell Transplant. 2013; 22:811-9], and pilot studies with large animal studies support their translation. The scaffold architecture has enabled the reversal of diabetes with 75 islets, which represents approximately ⅓ of the normal islet mass in the pancreas [Gibly et al., Biomaterials. 2011; 32:9677-84]. Decoration of the scaffolds with extracellular matrix (ECM) proteins enhances engraftment and function of transplanted islets, with the proteins seeming to directly impact the islet (enhanced viability, increased glucose stimulated insulin secretion) rather than impacting than host tissue integration (FIG. 1) [Salvay et al., Transplantation. 2008; 85:1456-64; Yap et al., Tissue Eng Part A. 2013; 19:2361-72]. Drug delivery from the scaffold has been investigated to modulate the local environment [Salvay et al., Gene Therapy. 2010; 17:1134-41; Avilés et al., Drug Delivery and Translational Research. 2011; 1:91-101; Boehler et al., Biomaterials. 2013; 34:5431-8; Gower et al., Adv Wound Care (New Rochelle). 2013; 2:100-6; Seidlits et al., Expert Opinion on Drug Delivery. 2013:1-11]. Layered scaffolds were developed that allowed for cell transplantation and localized delivery. The layered design allowed for independent tuning of the scaffold architecture that supports islet transplantation and protein release [Rives et al., Biomaterials 2009; 30:394-401]. Release of Exendin-4 significantly enhanced islet engraftment and function allowing for a reduction in the minimal mass of human islets needed to establish euglycemia [Hlavaty et al., American journal of transplantation: official journal of the American Society of Transplantation and the American Society of Transplant Surgeons. 2014; 14:1523-32]. Furthermore, localized delivery of anti-inflammatory factors can modulate the local immune response [Gower et al., Biomaterials. 2014; 35:2024-31; Boehler et al., Biotechnology and Bioengineering. 2014; 111:1210-21; Boehler et al., BioTechniques. 2011; 51:239-40, 42, 44 passim]. Strategies for local immunomodulation at the islet-loaded scaffold can be employed to limit or eliminate immune mediated destruction of islets in an autoimmune and allogeneic islet transplant models [Graham et al., Tissue Eng Part A. 2013; 19:1465-75]. Scaffold transplanted islets have been shown to be more susceptible to immune tolerance than intra-portally transplanted islets [Kheradmand et al., Biomaterials. 2011; 32:4517-24]. The microporous scaffold technology was tested first in non-human primate models with the transplantation of allogeneic islets (Example 3).

Example 3

Investigate Transplantation of Allogeneic Islets into the Peritoneal Fat on Microporous PEG Scaffolds for Long-Term Graft Function and Assess the Ability for Complete Graft Retrieval In this example, results with microporous scaffolds are extended to investigate the potential for complete graft retrieval in rodent models, as well as the transplantation and retrieval of allogeneic islets delivered on scaffolds using a non-human primate model. Prior studies using microporous scaffolds composed of poly(lactic-co-glycolide) (PLG) or PEG indicate that this platform supports the efficient transplantation, engraftment, and function of transplanted islets. Both material platforms have had similar efficacy in islet transplantation, and can be functionalized (i.e., ECM proteins, trophic factors) in analogous manners (described below and Example 4). PEG-based microporous scaffolds are investigated as the material is expected to have a decreased inflammatory response relative to PLG, have mechanical properties that are a better match with the omentum, and can be made non-degradable, thereby allowing retrieval if needed. Initial studies proposed herein will employ the microporous scaffolds to assess the retrievability of the islets at multiple time points following transplantation. These studies focus on a well-established material structure and composition that are implanted in a rodent model to assess the potential for graft retrieval in the short and long term post-transplantation. Second, these studies investigate the toxicology of these materials, which is necessary for regulatory approval. Furthermore, these microporous scaffolds are investigated in a non-human primate model to assess the functionality of the transplanted islets, and the host response and integration.

Retrievability of Islets Following Transplantation into the Peritoneal Fat

Figure 8:
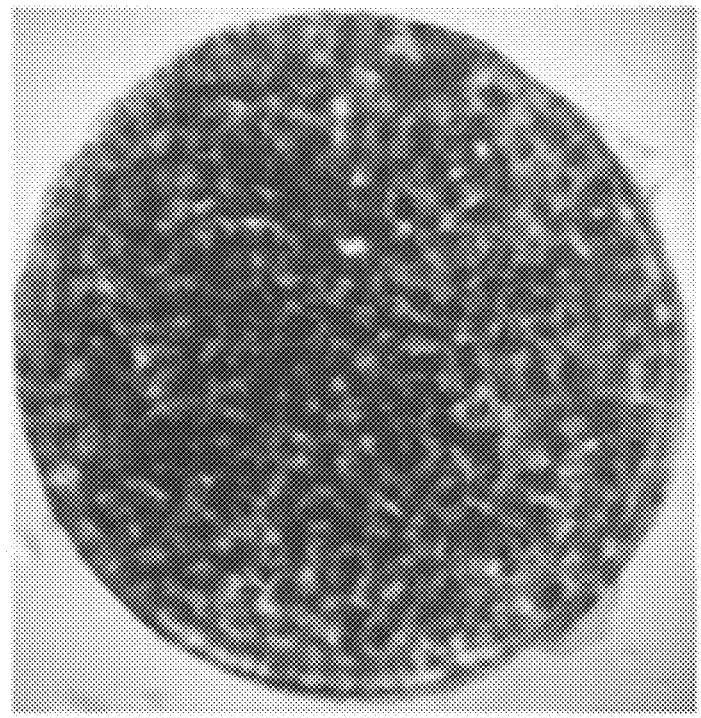
FIG. 8 shows a microporous PEG scaffold stained with Sirius red for the proposed transplants.

Microporous PEG scaffolds are formed as previously reported with slight modifications [Shepard et al., Biomaterials. 2012; 33:7412-21]. Briefly, PEG-maleimide (8-arm, molecular weight 20 kDa, 10% wt/wt) is formed in a saturated NaCl solution, mixed with NaCl crystals (diameter:250-425 µm) and a photoinitiator (1-2959), then cast into a mold (diameter: 5 mm, thickness 2 mm). The solution is irradiated with UV light to photo-crosslink the PEG-maleimide, and subsequently washed to remove the sodium chloride. Upon removal of the NaCl porogen, scaffolds are modified with collagen IV, which has significantly enhanced islet engraftment and function in our prior reports [Salvay et al., Transplantation. 2008; 85:1456-64; Yap et al., Tissue Eng Part A. 2013; 19:2361-72]. Collagen IV that is modified with thiol groups will be subsequently incubated with the scaffold so the thiols can react with the unmodified maleimide groups for immobilization to the surface. These scaffolds form consistent structures (FIG. 8), which have a high porosity that allows for rapid cell infiltration and ultimately vascularization of the islets following implantation.

Islets isolated from L2G85.Balb/c transgenic mice are transplanted on scaffolds into the fat pads of STZ-induced diabetic immunodeficient (NOD/SCID/Gamma, NSG) mice [Gibly et al., Cell Transplant. 2013; 22:811-9]. Blood glucose levels are monitored daily to determine normalization of blood glucose levels. Histological analyses are performed for scaffolds retrieved at multiple time points (1, 3, 6, 9, 12 months, n−12 each). The processing of the fat pad is investigated to ensure complete graft retrieval. Transplanted cells are identified by flow cytometry of GFP-expressing cells from the L2G85.Balb/c transgenic mice.

Toxicological Assessment of Microporous Scaffolds Following Transplantation and Testing of the Scaffold Extracts (Both Polar and Non-Polar) in In Vitro Assays and Multiple Animal Species Microporous PEG scaffolds were formed as described above, with the adaptation that the larger animals had scaffolds formed in a mold with a diameter of 3.6 mm. This size was selected as two scaffolds of this diameter can be employed to deliver sufficient islet numbers to the non-human primate, whereas 10 scaffolds can deliver sufficient islet numbers for the clinical trial. The PEG scaffold alone was tested in the omentum of cynomolgus monkeys. In addition, Guinea pigs, CD1 mice, and New Zealand Rabbits as described below. Device safety in vitro and in vivo were studied through a series of assays (designs of these studies specified in FDA Guide) that include hematological and histological analysis, as well as investigating the possibility of device failure, leaching, mutagenicity, sensitization and pyrogenicity.

Transplantation of Islet Loaded Microporous Scaffolds into Non-Human Primates

Non-Human Primate Transplantation:

As is now exemplified in Example 8, microporous scaffold testing in a non-human primate (NHP) model was begun immediately upon initiation of funding. The scaffolds are investigated in a non-human primate model to assess the host response to the gel and its components, islet function, and the potential for graft retrieval. First, the PEG scaffold alone is tested in the omentum of cynomolgus monkeys (n=3). Three scaffolds (approx. 3.6 cm in diameter, area: approximately 10 $cm^2$) per animal are inserted via a short periumbilical incision and placed laparoscopically on the omentum and attached with biomedical glue under general anesthesia. Implantation of the device alone is performed to determine scaffold safety in vivo and includes hematological and histological analysis, as well as investigating the possibility of device failure, leaching, sensitization and pyrogenicity. The scaffolds are retrieved after 6 months.

Initial transplantation studies will assess islet engraftment and function in non-diabetic recipients. Cynomolgus monkey islets are isolated using a collagenase enzyme, seeded on the scaffolds and transplanted into the omentum of 8 recipient cynomolgus monkeys (4 male; 4 female). One scaffold (3.6 cm diameter seeded with 2,500-5,000 EIN per $cm^2$) will be transplanted in each animal. As used herein, "EIN" refers to equivalent islet number. This number reflects that islets can be different sizes and that transplanting two small islets may be the same as transplanting 1 large islet—this reflects an adjustment for islet size.

Figure 9:
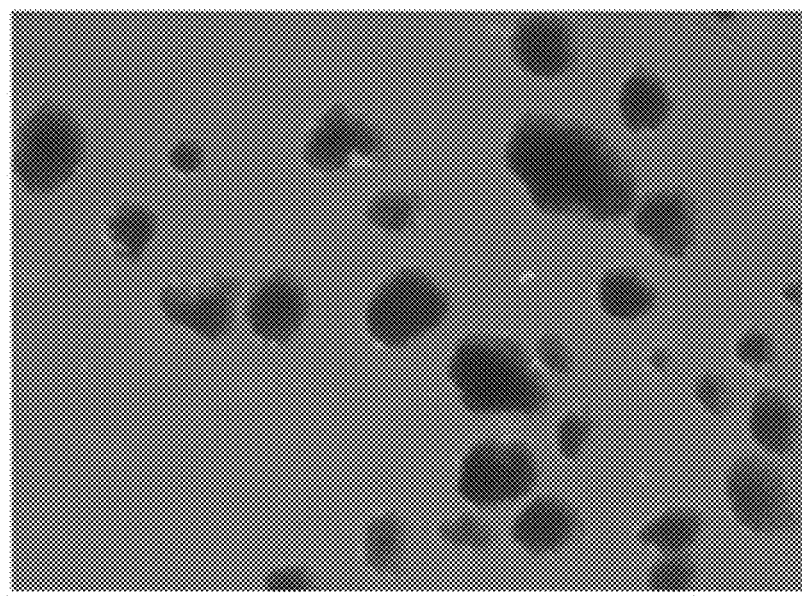
FIG. 9 shows isolated cynomolgus monkey islets stained with dithizone. Islets were isolated according to Qi et al., Pancreas. 2014; 43:226-35.

Furthermore, 8 sham surgeries are performed as controls (4 male; 4 female). UIC has previously developed a method of isolating high quality cynomolgus islets that will be used for the NHP islet isolation procedure (FIG. 9) [Qi et al., Pancreas. 2014; 43:226-35]. Following 6 months, the scaffold/islet combination will be retrieved and multiple tests performed on the islets including, viability, glucose stimulation and histological analysis. The presence of positive graft function will then allow for the testing of the scaffold and cynomolgus islets in a diabetic NHP model (n=8; 4 male; 4 female).

Figure 10:
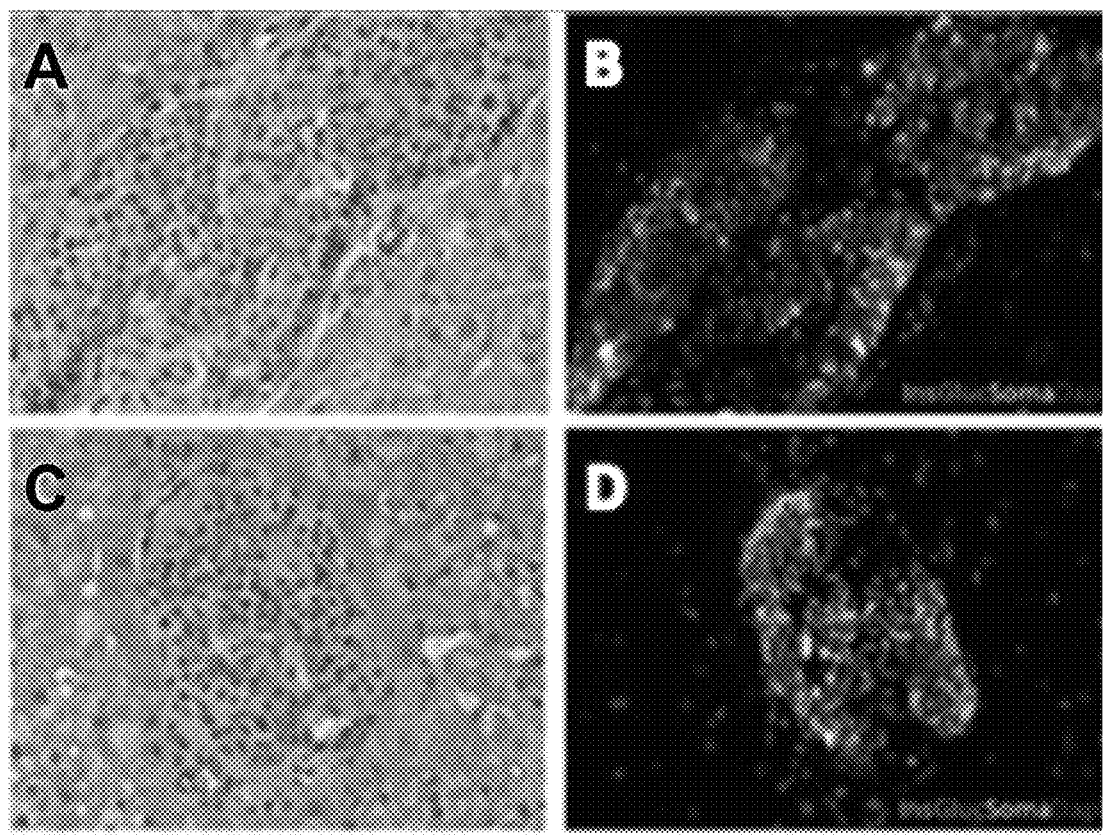
FIG. 10 shows H&E stain of liver engrafted human islets 30 days post transplantation into cynomolgus monkey (see A & C). Immunohistochemistry of liver engrafted human islets are shown 30 days post-transplantation into a cynomolgus monkey (see B & D); Insulin (green), glucagon (yellow), and somatostatin (red).

Subsequent studies will investigate transplantation into STZ-induced diabetic NHPs, which will be transplanted with 3 scaffolds (Each scaffold is approximately 10 $cm^2$ and seeded with 2,500-5,000EIN per gel (100,000 EIN total)) and graft function assessed through blood glucose monitoring and C-peptide levels. Hemoglobin A1c and fructosamine levels will also be followed. Intravenous glucose tolerance tests to determine islet cell function are also performed. Explanted tissue is analyzed histologically for the integration of the islet cells with the host tissue, and the host response to the graft. Histological and immunostaining are performed to determine the level of immune response, staining for T-cells, B-cells, NK cells, macrophages, as well as staining for insulin, glucagon and somatostatin. For all the aforementioned NHP experiments a human allo-based immunosuppressive drug regimen (sirolimus, tacrolimus, etanrecept and basiliximab cocktail) will be administered to prevent host rejection during intraportal cyno to cyno islet cell transplantation into STZ induced diabetic cynomolgus monkeys [Qi et al., Pancreas. 2014; 43:226-35]. This same immunosuppression protocol has also prevented rejection in human islet to cyno recipient transplant model with histological analysis of liver biopsies retrieved from diabetic cynomologus monkeys at 30 days post transplantation not indicating any signs of aggressive rejection or cellular infiltration, and human islet cells staining positive for all three major islet hormones; insulin, glucagon and somatostatin (FIG. 10). This result acts as a proof of concept for using naked cells on the scaffold in a NHP model. Together the rodent and NHP studies focus on a well-established material structure and composition.

It is expected that transplantation of islets on microporous PEG scaffolds in the omentum will result in long-term islet acceptance and glycemic control in diabetic NHPs. It is also expected that transplantation of islets in the omentum within a microporous scaffolds will enhance engraftment and function. It is further expected that the microporous scaffolds will be well-tolerated with minimal inflammatory responses.

Example 4

Investigate Transplantation hESC-Derived Insulin Positive Cells into the Peritoneal Fat on Microporous PEG Scaffolds for Long-Term Graft Function and Assess the Potential for Complete Graft Retrieval This example focuses on identifying the environmental effects on β-cell progenitor survival and differentiation following transplantation at multiple sites, and the role of vascularization in promoting maturation towards β-cells. Transplantation of β-cell progenitors into the kidney capsule has been the primary method by which these cells are able to survive, mature, and ultimately normalize blood glucose levels [Rezania et al., Diabetes. 2012; 61:2016-29; Rezania et al., Nature Biotechnology. 2014; 32:1121-33; Pagliuca et al., Cell. 2014; 159:428-39]. The ultimate translation of this strategy, however, will require transplantation at a clinically translatable site. While cell transplantation at alternative sites has led to maturation, insulin and C-peptide secretion, and normalized glucose levels by us and another laboratory [Weizman et al., Biomaterials Science. 2014; 2:1706-14], maturation of the transplanted cells appears less efficient than in the kidney capsule, which has the potential to be enhanced through designing the microenvironment and is the focus of this example [Salvay et al., Transplantation. 2008; 85:1456-64; Yap et al., Tissue Eng Part A. 2013 19(21-22):2361-72; Hlavaty et al., American Journal of Transplantation. 2014; 14:1523-32].

Herein, the real-time activity of key indicators of maturation toward mature β-cells are quantified in vivo as a function of the transplantation site. β-cell progenitors are modified with a transgene that can report on either i) the activity of transcription factors (TFs) that are associated with maturation or ii) the expression of genes indicative of mature β-cell function, which is achieved by using promoter regions that are specific for TFs or a particular gene that drive expression of luciferase. Bioluminescence imaging (BLI) is employed as a means to quantify the TF or promoter activity over time. Flow cytometry is employed to measure the relative distribution of progenitor and differentiated cell types within the transplant, which can be correlated with the TF or promoter activity. Measurements from implants within the kidney capsule will identify which reporters most directly correlate with in vivo β-cell maturation, while measurements from within the scaffold will indicate the how the peritoneal fat differentially stimulates the transplanted cells. Furthermore, how enhancing vascularization of the graft can influence the maturation of these progenitor cells is investigated.

Modulation of the local environment has the potential to augment the endogenous properties of the transplant microenvironment to enhance differentiation towards mature β-cells [Kelly et al., Nat Biotechnol. 2011; 29:750-6; Kroon et al., Nat Biotechnol. 2008; 26:443-52; Schulz et al., PLoS One. 2012; 7:e37004]. While one system demonstrated some enhancement of differentiation, the system involves undefined components (e.g., Matrigel) that render it unsuitable for translation [Kelly et al., Nat Biotechnol. 2011; 29:750-6; Kroon et al., Nat Biotechnol. 2008; 26:443-52; Schulz et al., PLoS One. 2012; 7:e37004]. The microporous scaffolds described herein have defined components that enable translation in contrast to the currently reported biomaterial systems for transplanting hESC-derived β-cell progenitors. Herein, defined factors are investigated that can be presented from PEG scaffolds, namely extracellular matrix proteins (collagen IV) and/or trophic factors (exendin-4) that are expected to directly influence the transplanted progenitor cells. Modifying this post-transplant microenvironment will significantly enhance the survival and differentiation of the β-cell progenitors, which will be characterized through luminescence reporter assays, flow cytometry, induction of normoglycemia, and an in vitro analysis of insulin-positive cells function.

β-Cell Progenitor Differentiation with Transplantation into the Kidney Capsule or Peritoneal Fat hESCs:

The hESC cell line used for culture of hESC-derived β-cell progenitors are H1 hESCs, purchased from WiCell (Madison, Wis.), which are on the list of FDA approved hESC lines, and previous reports have demonstrated their capacity for developing into insulin producing cells [Rezania et al., Diabetes. 2012; 61:2016-29; Rezania et al., Stem Cells. 2013 31(11):2432-42; Borowiak et al., Cell Stem Cell. 2009; 4:348-58; Chen et al., Nat Chem Biol. 2009; 5:258-65; Lammert et al., Mech Dev. 2003; 120:59-64; Lammert et al., Science. 2001; 294:564-7]. Culture conditions are as described in the art [Rezania et al., Nature Biotechnology. 2014; 32:1121-33]. β-cell progenitors were produced using the 7 stage culture protocol and the functional characteristics of these cells is presented in FIGS. 12 & 13. This characterization is consistent with the results presented by Rezania et al. [Nature Biotechnology. 2014; 32:1121-33].

Analysis of hESC-Derived β-Cell Function:

Several important cell parameters are measured to characterize the functionality of the beta-cell progenitors prior to in vivo testing. Such parameters include (1.) Compared to human islets, do the novel hESCs have similar physiological response profiles when exposed to glucose or other secretagogues? (2.) Do the hESCs have a normal or pathophysiological change in insulin stimulator-secretion coupling factors and what is their impact(s) on insulin secretion and functionality?

Figure 11:
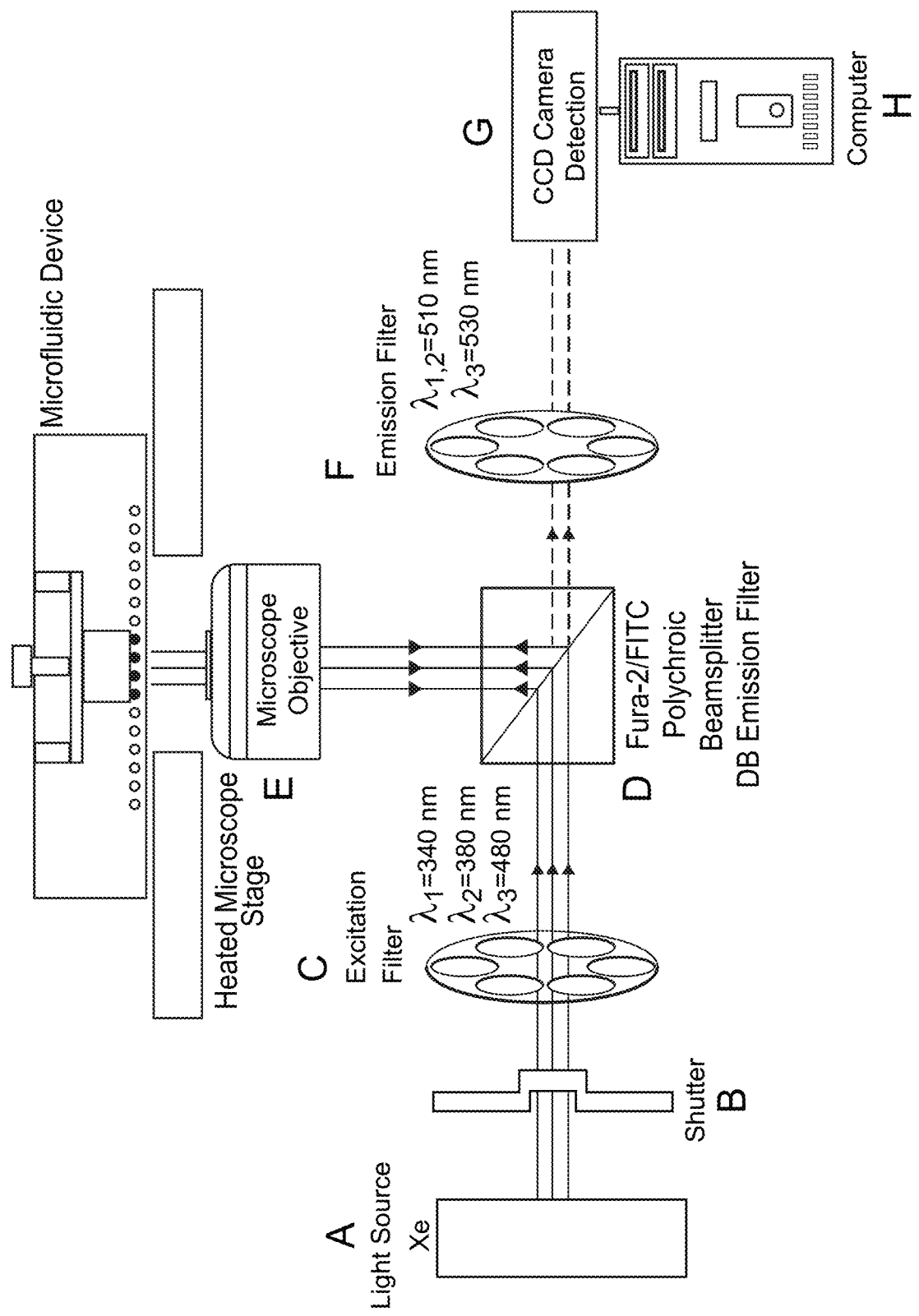
FIG. 11 depicts a schematic of a microfluidic perfusion and imaging system. Specifically depicted are: a Xenon arc lamp light source (A), shutter (B), excitation and emission filters (C and F), polychroic beamsplitter double emission filter (D), emission filters (E), CCD camera (G), and computer and imaging software (H).
Figure 12:
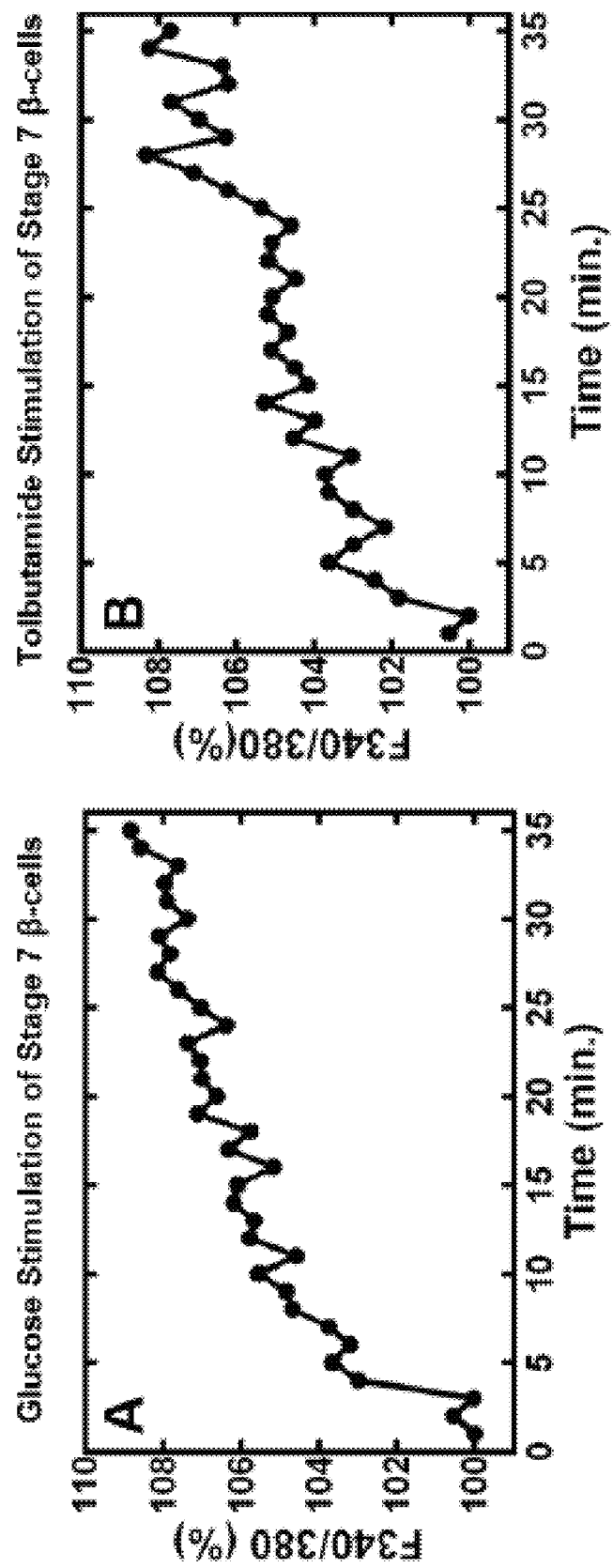
FIG. 12 shows the intracellular calcium profile of functional stage 7 β-cells during dynamic microperifusion assay on UIC's islet biochip. Specifically, (A) depicts the intracellular calcium profile in response to 20 mM glucose. (B) depicts Intracellular calcium profile in response to 150 µM Tolbutamide, a $K_{ATP}$ channel closer.
Figure 13:
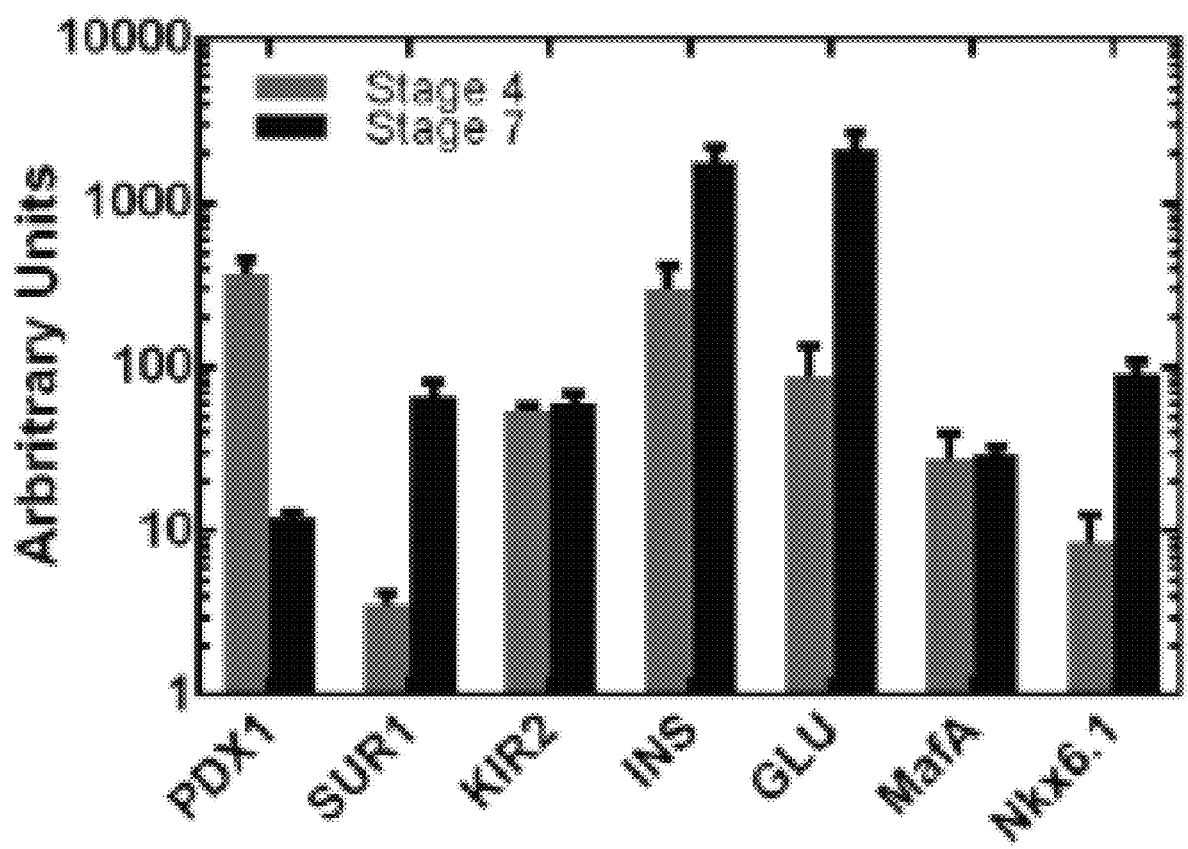
FIG. 13 depicts qRT-PCR of in vitro β-cell differentiation.

Simultaneous Measurement of $\Psi_m$, $[Ca^{2+}]_i$, NAD(P)H, and Insulin:

A microfluidic perfusion and imaging system is employed to systematically interrogate the physiology of the hESCs. The perfusion and imaging system is schematically depicted in (FIG. 11). The hESCs are incubated with 5 μM Fura-2AM (Molecular Probes, Inc.) and 2.5 μM Rh123 (Sigma) for 30 minutes at 37° C. in Krebs-Ringer buffer (KRB) and then placed into the temperature-controlled microfluidic device. Multiple cells are simultaneously observed with a 10× objective. Stimulation agents are then delivered by syringe pump. Dual-wavelength Fura-2/AM is excited at 340 and 380 nm and fluorescent emission is detected at 510 nm. Intracellular $Ca^{2+}$ is expressed as a ratio of fluorescent intensity F340/F380(%). Rh123 is excited at 490±10 nm, and emission is measured at 530±10 nm. Fura-2 and Rh123 fluorescence emission spectra are filtered using a Fura-2/FITC polychroic beamsplitter and double band emission filter (Chroma Technology. Part number: 73100bs). The reduced form of NAD and NADP, designated NAD(P)H, is measured using the same imaging system. The autofluorescence of NAD(P)H is excited at 365 nm and measured at 495 nm in dye-free islets. These images are collected with a CCD (Retiga-SRV, Fast 1394, QImaging). SimplePCI software (Hamamatsu Corp. location) is used for image acquisition and analysis. Perifusate samples are collected every minute for insulin determination using standard ELISA. The following experiments are performed on the hESCs prior to further in vivo investigation to ensure functionality and islet-like responses are present; Protocol 1. Determine hESCs function and glucose sensitivity by varying glucoses (8, 12, 16.7 or 25 mM) and 30 mM KCl. Protocol 2. Dissect the hESCs insulin stimulator-secretion coupling factors by verifying KATP channel activity using KATP channel closer (Tolbutamide) or opener (Diazoxide) or VDCCs activity using L-type calcium channel closer (Nifedipine). Protocol 3. Determine hESCs maximal insulin secretion capability and exhaustion by repetitive pulse glucose stimulation (four cycles of high glucose stimulations). Preliminary investigations were conducted to examine the functionality of β-cells differentiated in vitro according to a previously published protocol [Rezania et al., Nature Biotechnology. 2014; 32:1121-33]. Stimulation of stage 7 β-cells with either 20 mM glucose or 150 μM Tolbutamide, a $K_{ATP}$ channel closer, demonstrated that these cells are gluco-responsive and functional (FIG. 12).

qRT-PCR and Immunocytochemistry Analysis:

Successful differentiation into β-cells will be verified by immunocytochemistry by staining for insulin, glucagon, and somatostatin production as well as expression of markers which include Pdx1, C-peptide, and Nkx6.1. Furthermore, qRT-PCR is conducted to quantify the expression of key factors involved in the differentiation from hESCs to β-cells at multiple stages throughout the in vitro differentiation. Primers that include Pdx1, Sur1, Kir2, insulin, glucagon, MafA, and Nkx6.1 are used. Preliminary data from a differentiation (using a previously published protocol [Rezania et al., Nature Biotechnology. 2014; 32:1121-33]) indicated that cells successfully differentiate to immature β-cells as indicated in (FIG. 13), which is analogous to a previously published report [Rezania et al., Nature Biotechnology. 2014; 32:1121-33].

Transplantation of hESC-Derived β-Cell Progenitors:

Two conditions are investigated for transplantation: i) cells alone into the kidney capsule, and ii) cells seeded on a microporous scaffold. For transplantation into the kidney capsule, 5 million cells are implanted by pelleting cells and infusing them into the kidney capsule of streptozotocin-induced diabetic NSG mice, which are immunocompromised and will not reject the transplanted cells [Gibly et al., Cell Transplant. 2013; 22:811-9]. For the scaffold condition, cells are seeded onto scaffolds, which clusters the cells analogously to the kidney capsule. Scaffolds are fabricated as described herein [Salvay et al., Transplantation. 2008; 85:1456-64]. Scaffolds are seeded with 5 million cells and transplanted into the fat pads of mice as previously described [Gibly et al., Biomaterials. 2011; 32:9677-84; Salvay et al., Transplantation. 2008; 85:1456-64; Hlavaty et al., American Journal of Transplantation. 2014; 14:1523-32; Gibly et al., Cell Transplantation. 2013; 22:811-9; Blomeier et al., Transplantation. 2006; 82:452-9]. Note that each animal receives multiple implants: one implant in each kidney capsule and one implant in each fat pad. Hyperglycemic recipients are maintained on insulin pellets until we determine the amount of time necessary for the cells to secrete sufficient insulin (approx. 40-60 days). Blood glucose (Accu-Check) and c-peptide (ELISA) are measured three times per week by sampling blood from the tail vein.

Bioluminescence Imaging of In Vivo β-Cell Maturation:

Table 1 lists the lentiviral vectors that are employed for reporting on key TFs or genes associated with β-cell maturation. The TF binding sequences are designed based on the position weighted matrix (PWM) for binding of a TF to a DNA sequence [Siletz et al., Plos One. 2013; 8; Weiss et al., Integrative Biology. 2014; 6:1170-82]. Each reporter consists of three repeats of a TF-specific binding element driving the expression of fLuc and a puromycin resistance cassette used for the selection of infected cells prior to seeding cells to the scaffold for implantation [Duncan et al., Biotechnology and Bioengineering. 2014; 111:2082-94].

Release. 2015; 204:1-10]. Mice are injected intraperitoneally with D-luciferin (Molecular Imaging Products Company, Ann Arbor, Mich.) in PBS and imaged six minutes post-injection using the IVIS Imaging System. BLI is conducted daily for the first week following transplantation, and then 2× per week subsequently for the 40-day study. TF activity for each construct is imaged in a minimum of six mice.

Analysis of In Vivo Maturation of Transplanted β-Cell Progenitors:

The in vivo differentiation and maturation of β-cell progenitors to mature β-cells is examined by flow cytometry and immunohistochemistry. Scaffolds are retrieved, cells isolated, and flow cytometry is performed to quantify the number of insulin-, glucagon-, and somatostatin-positive cells. Furthermore, antibodies to MafA, NGN3, NeuroD, Pdx1, and Nkx6.1 are employed for comparison with the BLI measurements. Immunohistochemistry (IHC) is performed on scaffolds to validate the number of insulin-, glucagon-, and somatostatin-positive cells, and to determine

TABLE 1

Transcription factors for in vivo bioluminescence imaging of β-cell progenitor maturation.

| Transcription Factor | Function |
| --- | --- |
| MafA | an indicator of β-cell maturation; regulates insulin gene expression [Yamamoto et al., Journal of Biological Chemistry. 2013; 288: 21648-58; Lee et al., Diabetes. 2002; 51: 2546-51] and insulin secretion [Gao N, White P, Doliba N, Golson ML, Matschinsky FM, Kaestner KH. Foxa2 controls vesicle docking and insulin secretion in mature beta cells. Cell Metabolism. 2007; 6: 267-79] in mature β-cells in vivo. |
| Onecut1 | Aka HNF6; upregulated in pancreatic development; stimulates TFs Pdx1 and NGN3; negative regulator of MafA gene expression [Yamamoto et al., Journal of Biological Chemistry. 2013; 288: 21648-58] |
| NGN3 | required for expression of specific pancreatic TFs (NeuroD [Gradwohl et al., Proceedings of the National Academy of Sciences of the United States of America. 2000; 97: 1607-11]) |
| Nkx2.2 | regulates endocrine precursor cells; factor in β-cell development [Pauls et al., Developmental Biology. 2007; 304: 875-90]. |
| Nkx6.1 | regulates differentiation to pancreatic endoderm and an indicator of mature β-cells when co-expressed with MafA and Pdx1 [Pagliuca et al., Development. 2013; 140: 2472-83]. |
| Pdx1 | Aka insulin promoter factor 1 (Ipf1); regulates embryonic pancreatic development and β-cell maturation, survival, and activating insulin gene transcription [Stoffel et al., Genomics. 1995; 28: 125-6]. |
| NeuroD | Aka β2, acts jointly with Pdx1 and MafA, to regulate transcription of the insulin gene [Zhao et al., Journal of Biological Chemistry. 2005; 280: 11887-94]. |
| Msx2 | pancreatic development and regeneration [Krizik et al., Journal of Endocrinology. 1999; 163: 523-30]. |
| SUR1 | Pancreatic β-cell K/ATP channel subunits [Rezania et al., Stem Cells. 2013 31(11): 2432-42; Chen et al., Cell Reports. 2014; 6: 1046-58]. |
| KIR6.2 | Pancreatic β-cell K/ATP channel subunits [Rezania et al., Stem Cells. 2013 31(11): 2432-42: Chen et al., Cell Reports. 2014; 6: 1046-58]. |
| Promoter | |
| Rat insulin 2 | Regulates insulin gene transcription in functional, mature β-cells [Lu et al., Journal of Biological Chemistry. 1997; 272: 28349-59]. |
| CMV | constitutively active reporter; positive control determining viability [Qin et al., Plos One. 2010; 5]. |

Figure 14:
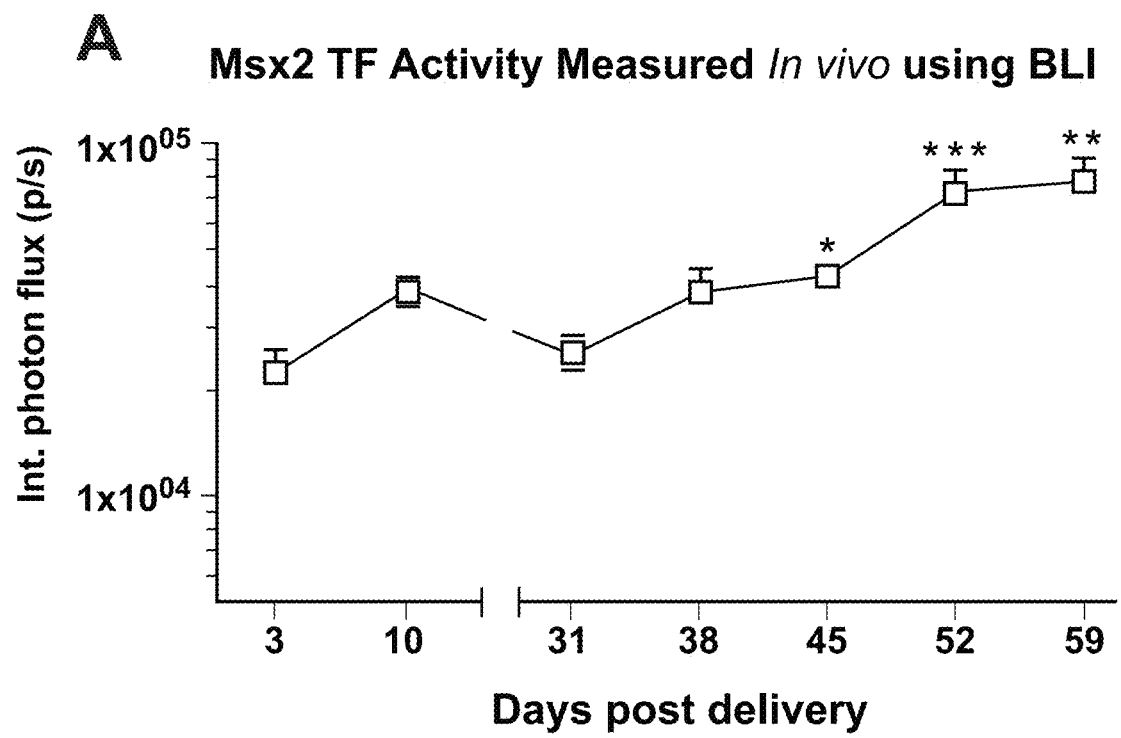
FIG. 14 depicts: (A) quantification of in vivo Msx2 TF activity over time, and (B) in vivo bioluminescence imaging of the rat insulin II promoter in transplanted islets 23 days post-transplant.
Figure 14:
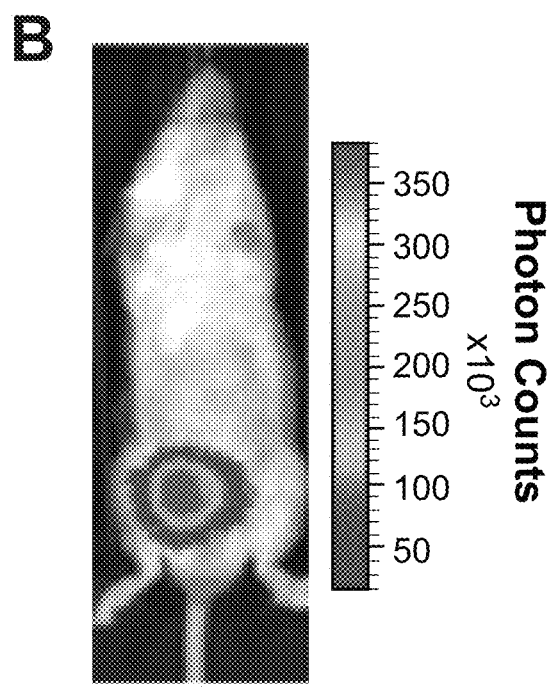
Figure 15:
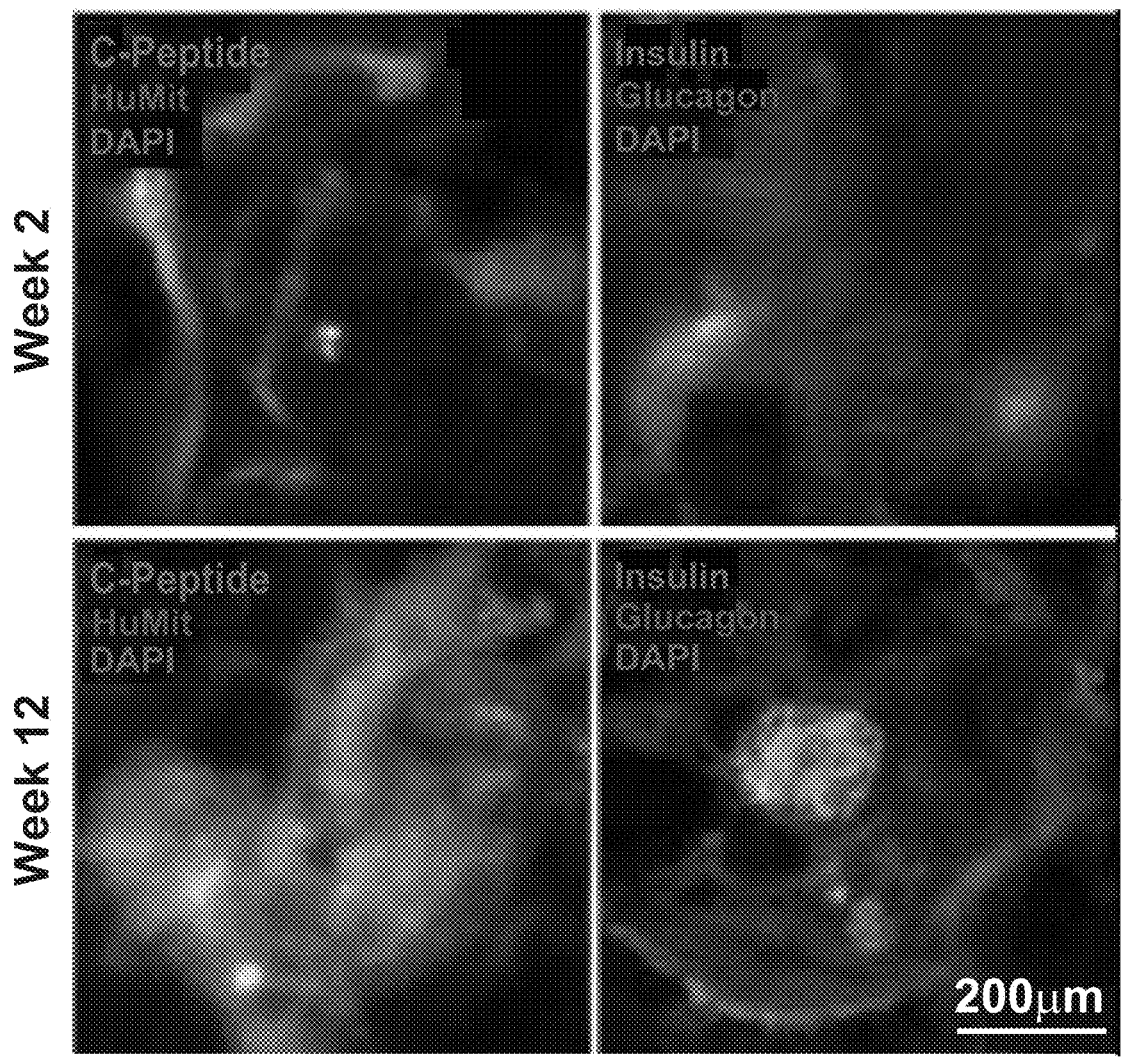
FIG. 15 depicts immunofluorescent staining of PEG scaffolds after 2 and 12 weeks of implantation in NSG mice.

Mice implanted with hESC-derived β-cell progenitors in the kidney capsule (cells alone) or into peritoneal fat (cells on scaffolds) are imaged to assess the activity of the TFs or the expression of differentiation markers. The ability of bioluminescence imaging to quantify the activity of a TF (Msx2, which has been implicated in pancreatic regeneration [Krizik et al., Journal of Endocrinology. 1999; 163:523-30]) (FIG. 14A), and the activity of insulin promoter (FIG. 14B) has been demonstrated [Blomeier et al., Transplantation. 2006; 82:452-9; Thomas et al., Journal of Controlled the percentage of cells that survive engraftment and mature in vivo, which is readily quantified using custom-designed image analysis software. Flow cytometry and IHC are conducted on a minimum of six mice for each condition. Preliminary studies have been conducted in which hESC-derived β-cell progenitors were seeded to PEG scaffolds and implanted within the epididymal fat pads of NSG mice. IHC was conducted 2 and 12 weeks post-transplant and cells were stained for C-peptide, human mitochondria (HuMit), insulin and glucagon, including a DAPI counterstain (FIG.

Figure 16:
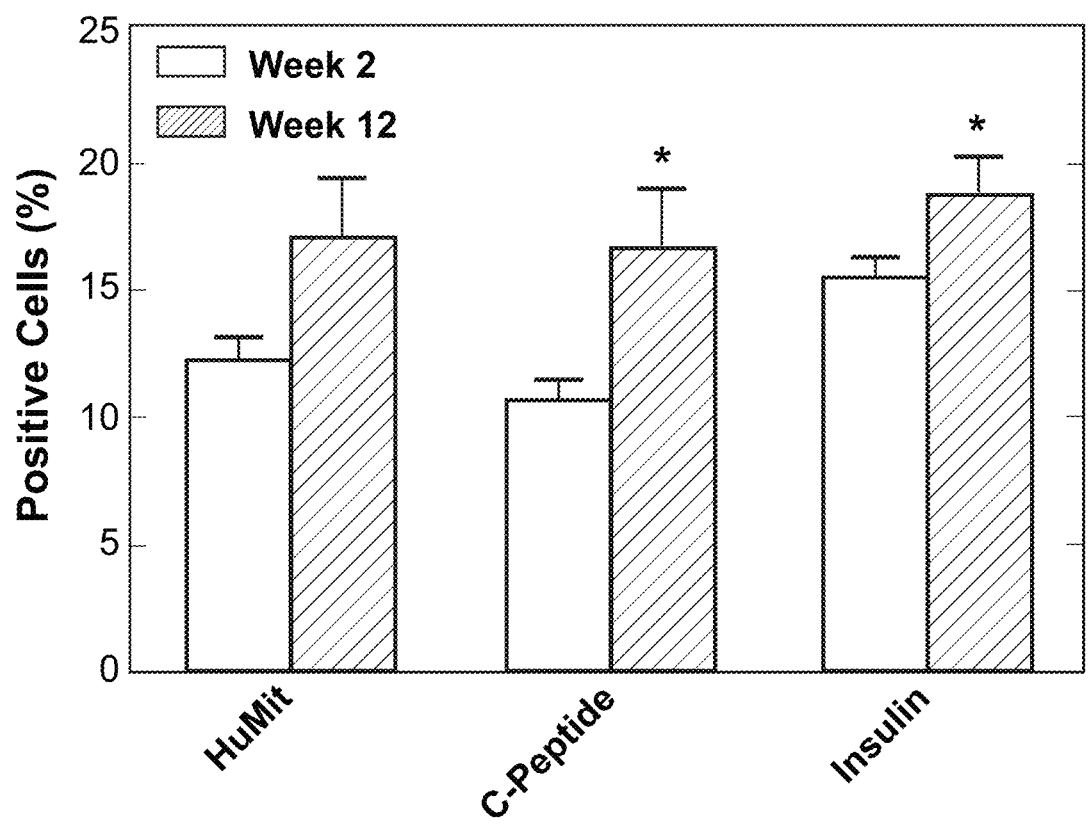
FIG. 16 shows a bar graph depicting the quantification of immunohistochemistry images of whole sections for entire scaffolds that were removed at 2 and 12 weeks post-transplantation (p<0.05).

15). Qualitatively, co-localization of both HuMit and C-peptide stains as indicated by the yellow color at both weeks 2 and 12, indicate that human cells are present within the scaffold and producing C-peptide. Additionally, the insulin and glucagon stains indicate that cells were more polyhormonal, with fewer insulin-producing cells after 2 weeks compared to an increase in monohormonal insulin-producing cells after 12 weeks. Furthermore, after sectioning entire scaffolds that were removed from mice, whole sections were imaged for the entire thickness of the scaffold to comprehensively quantify the expression of HuMit, C-peptide, and insulin (FIG. 16). The IHC quantification analysis determined that both C-peptide and insulin production significantly increased between 2 and 12 weeks (p<0.05), while the percentage of HuMit-positive cells was not found to significantly increase (n.s. p=0.05). Therefore, this data show that transplanted β-cell progenitors did not significantly proliferate over the course of 10 weeks, but rather the existing cells matured in vivo as indicated by the significant increases in C-peptide and insulin production.

Since the cells originate as pluripotent hESCs, the safety profile for transplanting these progenitor cells is also evaluated. This analysis is performed alongside the flow cytometry and IHC described above. For flow cytometry, upon removal of the scaffold, the fat pads are digested and analyzed for the presence of human cells. IHC enables visualization of both the scaffold and fat pad, and looks for the presence of human cells or teratoma formation. Markers for human mitochondrial surface antigen are used to distinguish human cells from mouse cells. The safety profile will be investigated on a minimum of 12 mice.

β-Cell Progenitor Differentiation on VEGF-Releasing Scaffolds:

It is contemplated herein to locally deliver the angiogenic factor vascular endothelial growth factor (VEGF) in order to promote vascular infiltration, as endothelial cells of the vessels secrete factors critical for endocrine differentiation in vivo in the mouse foregut endoderm [Lammert et al., Mech Dev. 2003; 120:59-64; Lammert et al., Science. 2001; 294:564-7; Villasenor et al., Semin Cell Dev Biol. 2012; 23:685-92], suggesting that signals from host endothelial cells may also provide cues for maturation of the hESC-derived β-cell progenitors. The effect of endothelial cells is supported by studies that observed infiltration of the host vasculature [Bruin et al., Diabetologia. 2013 56(9):1987-98], which was suggested to have contributed to cell maturation. The interaction between the host vasculature and the graft also allows for the influx of nutrients and trophic signals to infiltrate the graft, possibly enhancing survival and function [Lammert et al., Curr Biol. 2003; 13:1070-4]. While islets transplanted on microporous scaffolds are well vascularized [Blomeier et al., Transplantation. 2006; 82:452-59] (FIG. 1B), localized delivery of VEGF enhances the rate and extent of vascularization. Of note, encapsulation systems that restrict immune cells also prevent vascularization, and thus the potential for endothelial cells to enhance maturation is not captured.

Figure 17:
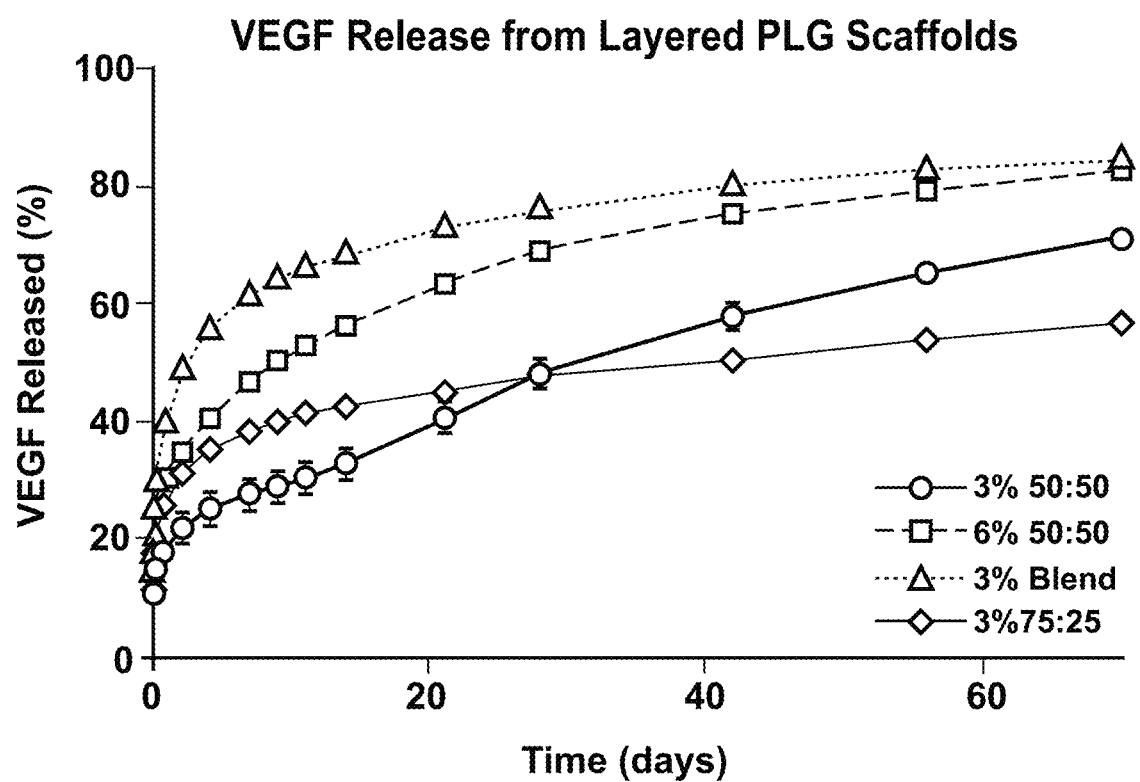
FIG. 17 depicts a graph of VEGF release from layered PLG scaffolds.

Microporous scaffolds releasing VEGF are formed using a layered architecture (FIG. 3A). The inner layer is designed for controlled release [Hlavaty et al., American Journal of Transplantation. 2014; 14:1523-32], while the outer layer is highly porous and allows for cell transplantation as well as infiltration of host tissue. The microporous scaffolds are formed by casting the gel around a VEGF inner layer which is delivered locally from the scaffold to enhance vascularization and examine the impact on progenitor cell maturation. The ability for sustained VEGF release has been demonstrated (FIG. 17), and 1 µg of VEGF is delivered that is released over approximate 30 days, which has promoted robust vascularization of scaffolds. The extent of vascularization will be quantified using immunohistochemistry by staining for lectin [Gibly et al., Biomaterials. 2011; 32:9677-84]. To quantify vascularization, IHC images are analyzed using NIH ImageJ by counting the amount of lectin-positive pixels and the amount of cells that are lectin-positive. The activity of specific pathways and fate of the transplanted β-cell progenitors is analyzed as described herein (BLI, IHC, flow cytometry).

Trophic Factor Delivery to Enhancement of β-Cell Progenitor Differentiation.

Figure 18:
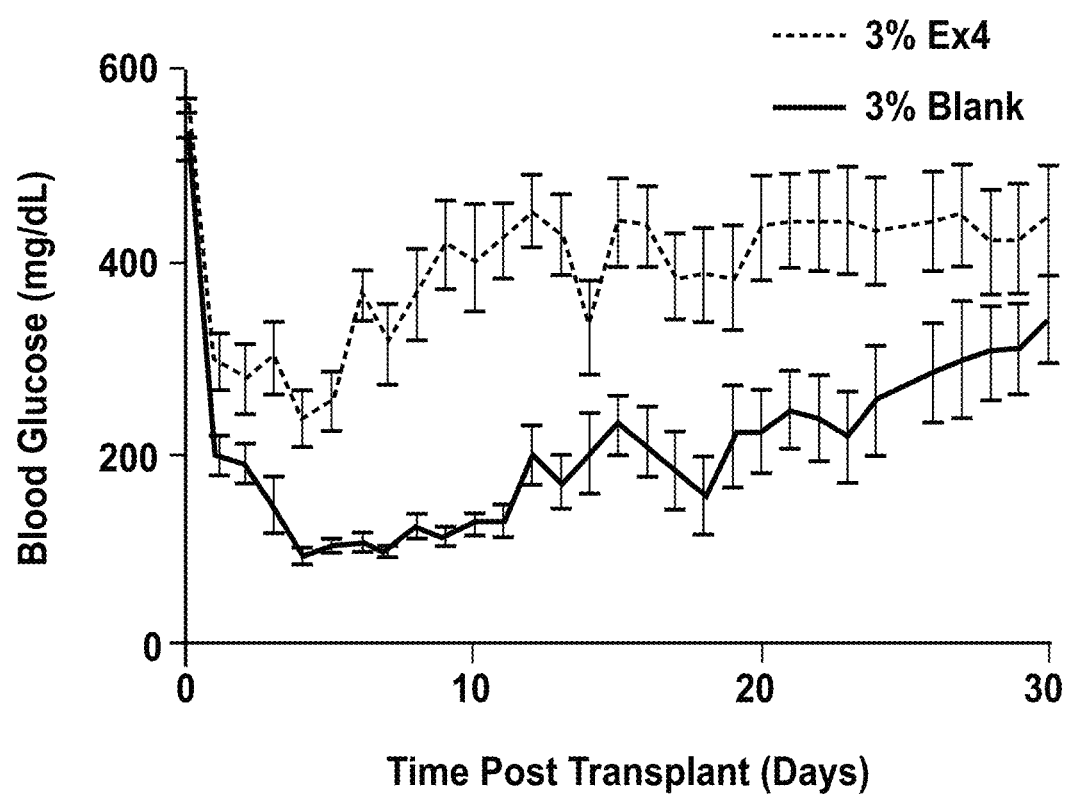
FIG. 18 shows a graph of blood glucose measured over time from mice transplanted with 1500-1800 IEQ on 3% Ex-4 and blank scaffolds.

Localized delivery of trophic factors released from scaffolds provides the transplanted cells with the cues necessary for enhanced survival and function. The localized delivery of Ex4 to enhance engraftment and function of transplanted human islets has been investigated. In vitro release studies demonstrated the ability for sustained release of peptides for months, and Ex4 delivery supported a 25% reduction in the minimal islet mass to restore euglycemia (FIG. 18). Additional studies demonstrated that Ex4 release to transplanted β-cell progenitors decreased blood glucose levels (FIG. 18) and significantly increased C-peptide production relative to blank control scaffolds (0.6±0.1 ng/mL c-peptide in mice with Ex4 and 0.3±0.1 ng/mL in mice containing blank control scaffolds; p<0.05). An increase in the ratio of insulin$^+$ to glucagon$^+$ cells by IHC was also noted. These results strongly support the potential of Ex4 to enhance the in vivo maturation of the progenitor cells toward mature β-cells. Delivery of 2 µg and 5 µg that is released over approximately 40 days is also investigated, which is the release profile that was used for human islet transplantation (FIG. 2, [Hlavaty et al., American Journal of Transplantation. 2014; 14:1523-32]) and is a time that corresponds with that required for β-cell progenitors to induce normoglycemia following transplantation [Rezania et al., Nature Biotechnology. 2014; 32:1121-33]. The analysis of the graft is performed as described herein.

Expected Outcomes.

No problems with fabrication and transplantation of these scaffolds is expected as the techniques are known [Gibly et al., Biomaterials. 2011; 32:9677-84; Salvay et al., Transplantation. 2008; 85:1456-64; Yap et al., Tissue Eng Part A. 2013; 19:2361-72; Gibly et al., Cell Transplantation. 2013; 22:811-9; Blomeier et al., Transplantation. 2006; 82:452-9; Jang et al., Expert Review of Medical Devices. 2004; 1:127-38]. For in vitro differentiation of hESCs, techniques are known in the art [Rezania et al., Diabetes. 2012; 61:2016-29; Rezania et al., Nature Biotechnology. 2014; 32:1121-33; Rezania et al., Stem Cells. 2013 31(11):2432-42]. BLI of in vivo cell maturation enabled quantification of the real-time activity of key TFs and protein expression associated with the maturation of β-cells, and revealed the efficiency of β-cell maturation with respect to various transplant environments and environmental cues. If the reporters specified for BLI were not sufficiently sensitive or noisy, the NanoLuc reporter, which has previously been shown to have increased sensitivity for in vivo imaging, was used [Stacer et al., Molecular Imaging. 2013; 12]. Delivery of VEGF was expected to function indirectly by enhancing vascularization of the scaffold, which provides nutrients to enhance cell survival and endothelial cells then interact with the hESC-derived β-cell progenitors to provide signals necessary to promote maturation. The dose or release rate of VEGF was adjusted as necessary (FIG. 17) if vascularization needed further enhancement. It is expected that this cell transplantation will be safe, with no progenitor cells observed and also transplanted cells present only within the scaffold. If cells were observed in the fat pad then a systemic distribution of the cells (blood, spleen, liver, lungs) was investigated. In the unlikely event that pluripotent cells were observed following transplantation, flow cytometry was employed to sort and purify cells prior to transplantation. CD142 has been previously used, as it is expressed on the surface of pancreatic endoderm cells within the population of differentiated hESCs that ultimately mature into all functional pancreatic cell types upon transplantation in mice [Kelly et al., Nat Biotechnol. 2011; 29:750-6].

ECM proteins on scaffolds were expected to aid in cell maturation by mimicking the basement membrane found in the pancreas, thereby facilitating cell-matrix interactions necessary for enhanced cell maturation. It was possible that ECM proteins may not be sufficient to promote maturation of hESC-derived β-cell progenitors and that trophic factors may be necessary. Thus, delivering trophic factors such as Ex4 enhance differentiation of the β-cell progenitors and the establishment of euglycemia more rapidly than in the absence of factors. Furthermore, besides the delivery of endogenous trophic factors, a proposed alternative is the co-transplantation of pancreatic mesenchyme and/or mesenchymal stem cells that have previously been shown to enhance β-cell maturation through the endogenous release of trophic factors [Attali et al., Diabetes. 2007; 56:1248-58; Baertschiger et al., Pancreas. 2008; 37:7584; Bianchi et al., Journal of the Peripheral Nervous System. 2014; 19:S3-S; Duvillie et al., Diabetes. 2006; 55:582-9; Landsman et al., Plos Biology. 2011; 9; Sneddon et al., Nature. 2012; 491: 765-8]. Furthermore, quantification of TF that may be differentially active between the peritoneal fat and kidney capsule sites suggested factors that could target the TFs or the associated signaling pathways as a means to enhance maturation.

Example 5

Investigate Allogeneic Islet Transplantation Using a Microporous Scaffold Placed onto the Omentum of Brittle, Type I Diabetic Patients with the UIC Protocol of Immunosuppression Rationale:

Intraportal islet transplantation provokes an instant blood mediated inflammatory reaction that leads to significant, immediate islet cell loss. Using the omentum as a transplant site with a microporous scaffold could reduce the need for using multiple donors to achieve long-term insulin independence after islet transplantation. Additionally, these investigations deliver important clues on whether this transplant site and the use of scaffolds provide a safe, retrievable site for future, hESC-derived islet cell transplants into brittle, type I diabetic patients.

Briefly, a pilot trial is to be performed with three, brittle, type I diabetic patients presenting with severe, hypoglycemic unawareness qualifying for islet transplantation using UIC's immunosuppressive protocol [Gangemi et al., Am J Transplant. 2008; 8:1250-61; Vaithilingam et al., Tissue Eng Part A. 2014; 20:324-34]. The foldable scaffold is to be loaded with purified, human islets at a dose of a minimum of 5000 IEQ/kg body weight at a seeding density of 5000 EIN per $cm^2$ of scaffold, and then placed laparoscopically on the omentum of the recipients. Patients will receive the UIC protocol of immunosuppression as previously described and are monitored. At the end of 6 months, the patient will undergo a diagnostic laparoscopy for macroscopic inspection of the abdominal cavity and evaluation of the transplant site.

This example provides a stepwise, methodological approach to the use of microporous scaffolds (e.g., PEG scaffolds) for transplantation of allogeneic islets and ES-derived insulin positive cells into the omentum.

Example 6

Figure 19:
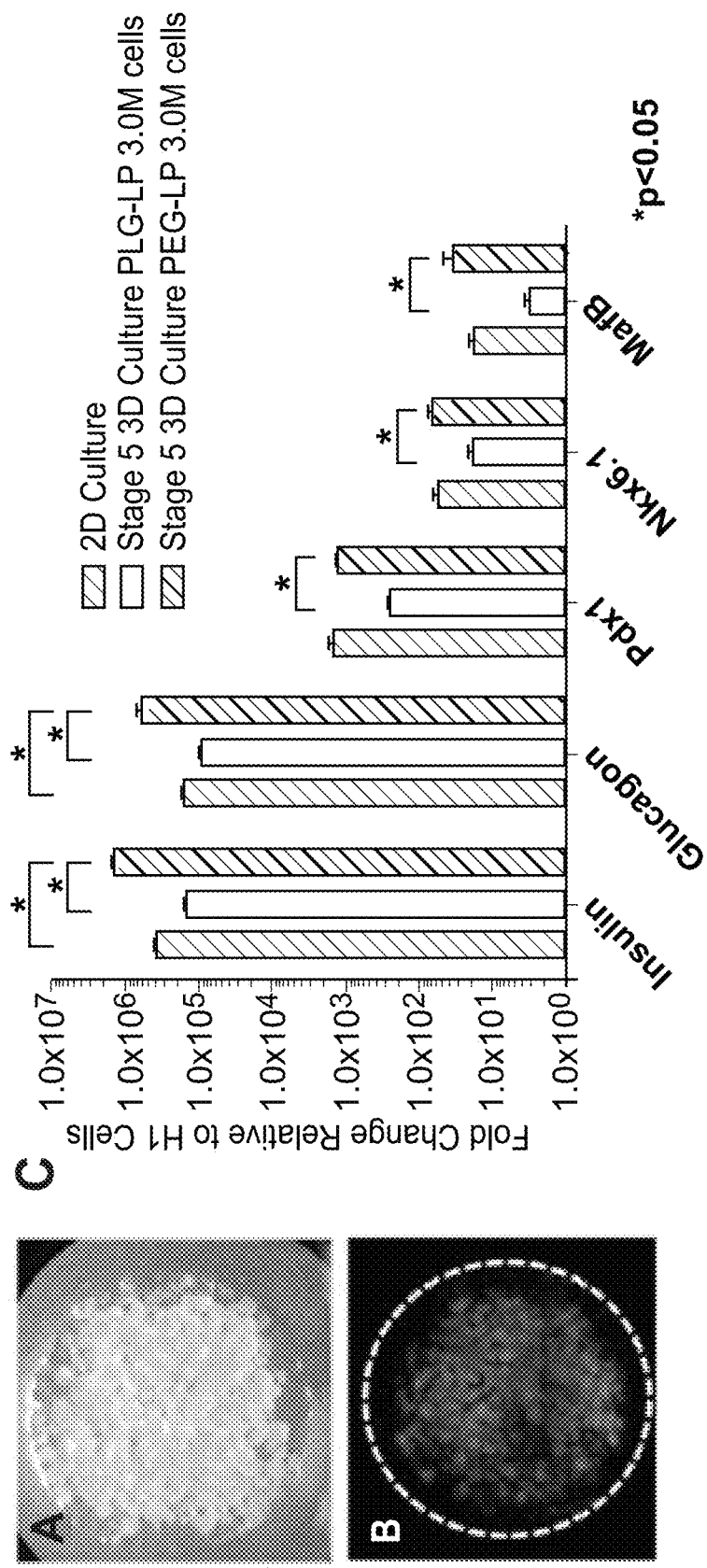
FIG. 19 shows in vitro beta-cell progenitor differentiation using three-dimensional PEG and PLG scaffold matrices. In stage four of beta cell differentiation from pluripotent human embryonic stem cells, pancreatic progenitors were seeded to PLG and PEG scaffolds and allowed to mature through stage five, in vitro. Stereo micrograph of pancreatic progenitors seeded to PEG scaffold (A). Live/dead stain of pancreatic progenitor cells seeded to PEG scaffold (B). qRT-PCR for mature pancreatic markers conducted on stage 5 pancreatic endocrine cells cultured traditionally in two-dimensional, monolayer culture, seeded on large pore PLG scaffolds, and seeded on large pore PEG scaffolds (C).
Figure 20:
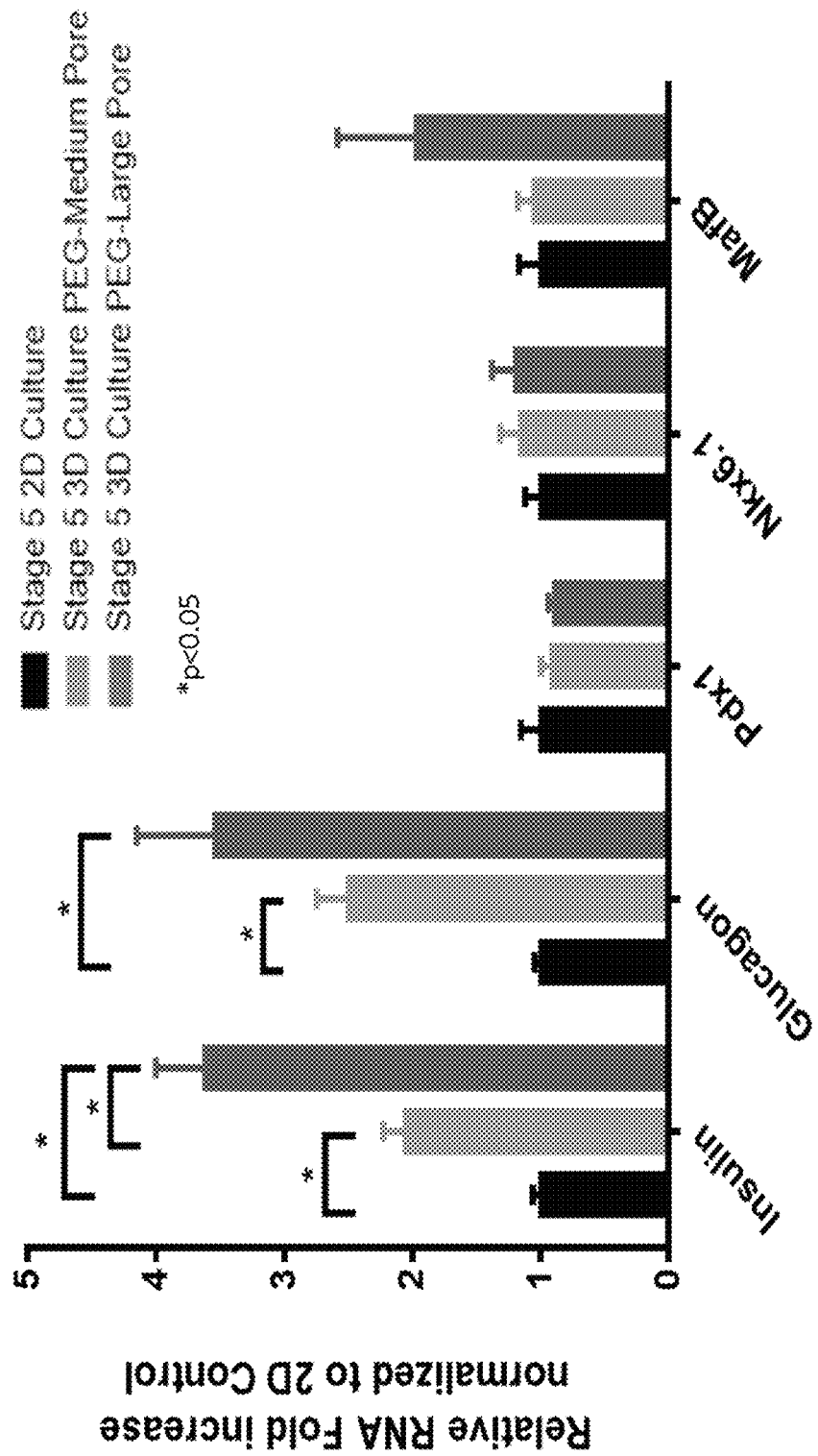
FIG. 20 depicts in vitro beta-cell progenitor differentiation comparing medium pore size (250-425 um) PEG scaffolds to large pore size (500-600 um) PEG scaffolds. In stage four of beta cell differentiation from pluripotent human embryonic stem cells, pancreatic progenitors were seeded to medium pore size and large pore size PEG scaffolds and allowed to mature through stages five, in vitro. Quantitative reverse transcriptase polymerase chain reaction (qRT-PCR) was conducted for mature pancreatic markers on stage 5 pancreatic endocrine cells cultured traditionally in two-dimensional, monolayer culture, seeded on medium pore size PEG scaffolds, and seeded on large pore size PEG scaffolds (C).

Comparison Between Differentiation of Human Pancreatic Progenitor Cells to Immature Beta Cells Seeded to PLG and PEG Scaffolds with Varying Pore Sizes Human embryonic stem cells were differentiated to pancreatic progenitor cells in a traditional two-dimensional, monolayer culture. Cells were then dissociated and seeded to PEG or PLG scaffolds with large pore sizes (500-600 um). As evidenced by light microscopy (FIG. 19A), the pancreatic progenitors seeded to PEG scaffolds self-assembled within the pores into islet-like clusters. Cells remained viable upon self-assembly when seeded to PEG scaffolds as indicated by a live (green)/dead (red) stain (FIG. 19B). After cells were differentiated to pancreatic endoderm cells, qRT-PCR was conducted (FIG. 19C) on cells differentiated in traditional two-dimensional, monolayer culture, cells seeded to large pore PLG scaffolds, and cells seeded to large pore PEG scaffolds. For all mature beta cell markers analyzed, cells seeded to large pore PEG scaffolds had significantly increased expression of mature beta cell markers compared to cells seeded to large pore PLG scaffolds ($p<0.05$) and for insulin and glucagon compared to two-dimensional culture ($p<0.05$). Furthermore, the influence of PEG scaffold pore size on cell differentiation was analyzed by qRT-PCR for mature beta cell markers (FIG. 20), and these results indicated the cells seeded to large pore scaffolds had significantly increased expression of insulin and glucagon, compared to cells seeded to medium pore (250-425 um) scaffolds and cells in two-dimensional monolayer culture.

These results indicate that cells can self-assemble within PEG scaffolds and that cell differentiation within PEG scaffolds is more efficient compared to cells seeded to large pore PLG scaffolds and cells in two-dimensional culture. Additionally, cell differentiation is affected by the pore sizes of the PEG scaffolds, with large pore PEG scaffolds facilitating the most efficient differentiation to pancreatic endoderm cells.

Example 7

Figure 21:
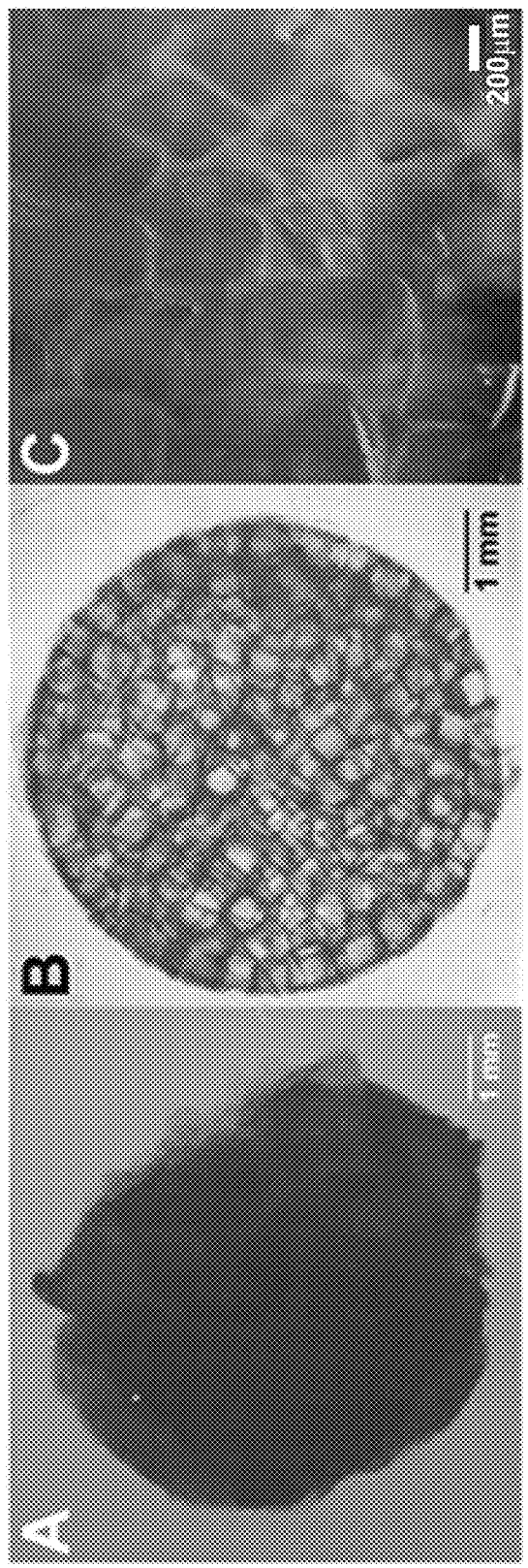
FIG. 21 depicts encapsulating and microporous hydrogels for islet transplantation. (A) 10% (wt/vol) bulk PEG hydrogels were fabricated to encapsulate islets. (B, C) Microporous gel for islet seeding. Gels were stained with sirius red for visualization.
Figure 22:
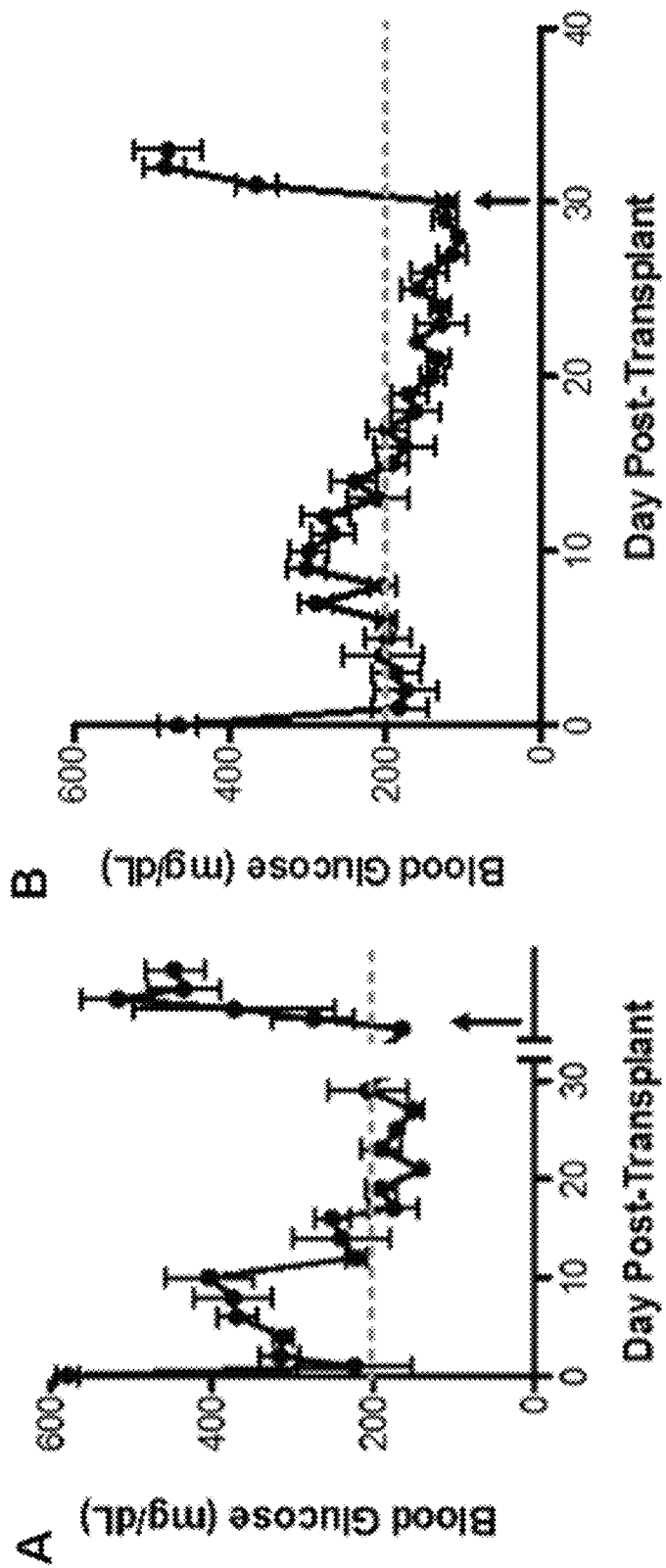
FIG. 22 shows blood glucose monitoring post-transplant with hydrogel materials in fat pad transplantation site of diabetic mice. (A) Bulk, non-degradable encapsulating hydrogels with 700 IEQ reversed diabetes in recipient mice, with consistent normoglycemia achieved by 3 weeks post-transplant (n=3, ±SEM). (B) Salt-leached, microporous hydrogels seeded with 700 IEQ displayed consistent normoglycemia by 3 weeks post-transplant (n=5 pre-graft removal, n=4 post-graft removal, ±SEM). Recipient mice in both groups reverted to a diabetic state within 2-4 days following hydrogel removal (indicated with a black arrow).
Figure 23:
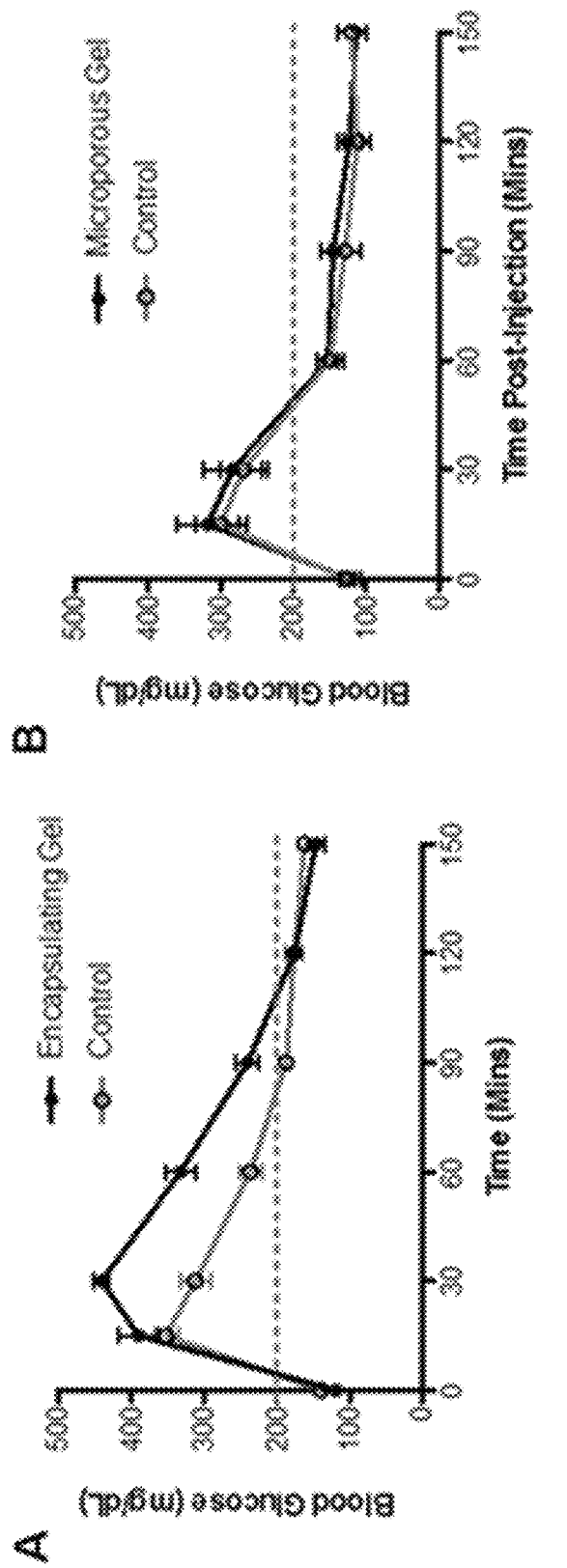
FIG. 23 shows glucose responsiveness of encapsulating and microporous hydrogels 1 month post-transplantation. In (A), post-injection, normoglycemic blood glucose levels (<200 mg/dL) were achieved by the encapsulating (n=5, ±SEM) and control (n=9, ±SEM) groups at 120 and 90 minutes, respectively. An area under the curve analysis indicated statistical significance at 30 minute (p=0.0061), 60 minute (p=0.0007), and 90 minute time points (p=0.0005). In (B), post-injection, normoglycemic blood glucose levels were achieved by the microporous (n=5 pre-graft removal, n=4 post-graft removal, ±SEM) and control (n=4, ±SEM) groups at 60 minutes. An area under the curve analysis indicated no statistical significance at any time point. IPGTTs were performed 1 month post-transplantation, between Day 30-35.

Transplantation of Syngeneic Mouse Islets to Mouse Epididymal Fat Pads Either Encapsulated within PEG Hydrogels or Seeded to Microporous PEG Hydrogels In this example, encapsulating PEG hydrogels (FIG. 21A) and microporous PEG hydrogels (FIGS. 21B, 21C) were fabricated and the polymer was stained using Sirius Red for visualization of porous scaffold structures. The images indicate that microporous PEG hydrogels contain pores and inter-pore connectivity (a distinct feature of the hydrogel technology provided herein) for islets to reside within (polymer stained red; pores are white/transparent void spaces). Conversely, the encapsulating PEG hydrogel (FIG. 21A) lacks porous structures. Syngeneic mouse islets were isolated and either encapsulated within encapsulating PEG hydrogels or seeded to marcoporous PEG scaffolds and transplanted to the epididymal fat pads of immunocompetent, diabetic C57 mice. Blood glucose monitoring following transplantation (FIG. 22) indicates that in days 1-15 following transplantation, islets encapsulated within PEG hydrogels (FIG. 22A) did not immediately reverse hyperglycemia, whereas islets seeded to microporous PEG hydrogels (FIG. 22B) immediately rendered the diabetic mice euglycemic (blood glucose levels <200 mg/dL) in the days following transplantation. Furthermore, glucose responsiveness of the transplanted islets was evaluated by conducting an in vivo glucose tolerance test comparing encapsulated islets and islets seeded to microporous PEG scaffolds against non-diabetic control mice (FIG. 23).

These results indicate that islets encapsulated within PEG hydrogels (FIG. 23A) did not respond to the glucose stimulus as well as non-diabetic control mice, where islets seeded to microporous PEG scaffolds (FIG. 23B) had a similar degree of responsiveness to the glucose stimulus compared to the non-diabetic control mice. Together, this data demonstrate that, in vivo, syngeneic mouse islets seeded to microporous PEG scaffolds have increased function compared to islets encapsulated within PEG hydrogels.

Example 8

Figure 24:
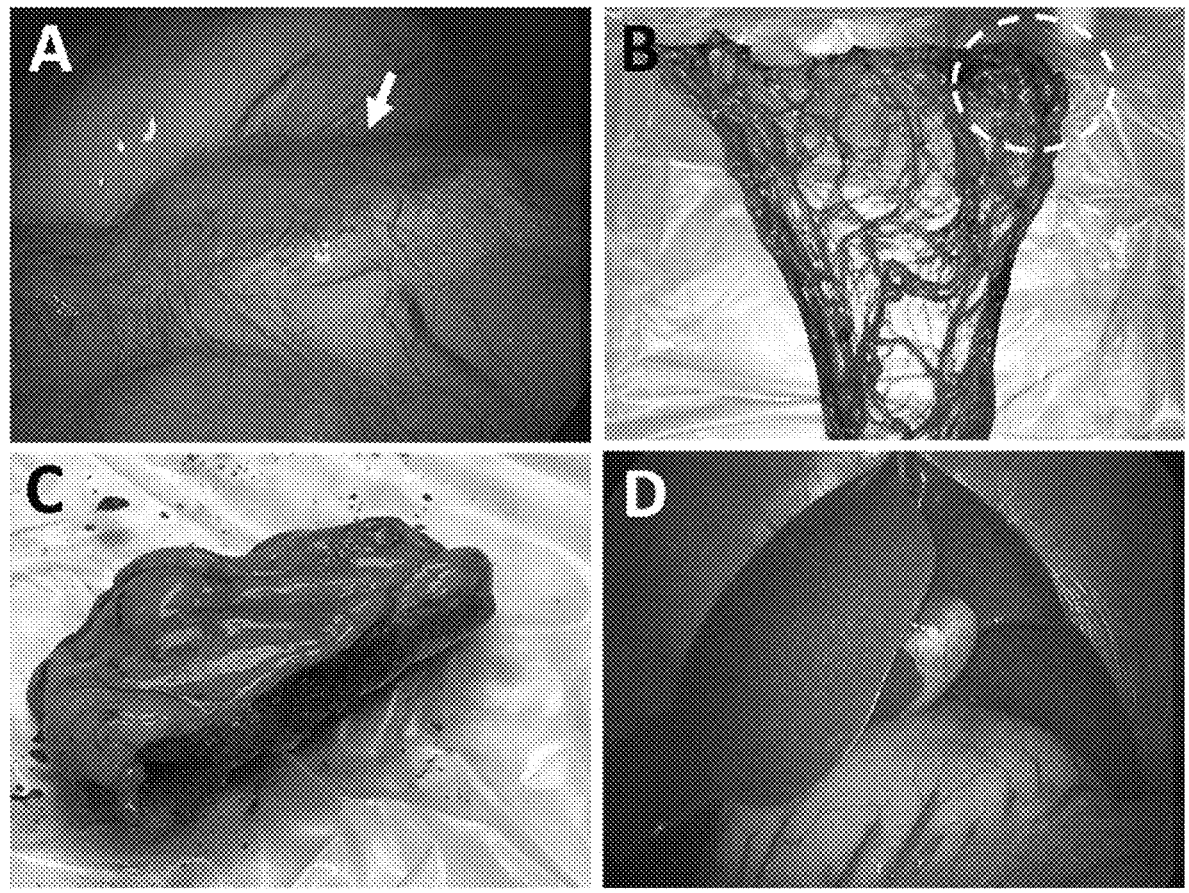
FIG. 24 depicts scaffold and bursa omentalis removal from a non-human primate (NHP) 30 days following transplantation. Laparoscopically, a camera was inserted into the peritoneal cavity to observe the implanted scaffold (white arrow) in vivo. Presence of neo-vasculature was observed (A). The bursa omentalis was removed to observe gross tissue morphology (B) (scaffold delineated by white circle). Cross-section of the retrieved scaffold (C). Laparoscopic image of the liver shows no spotting in reaction to the presence of the scaffold (D).
Figure 25:
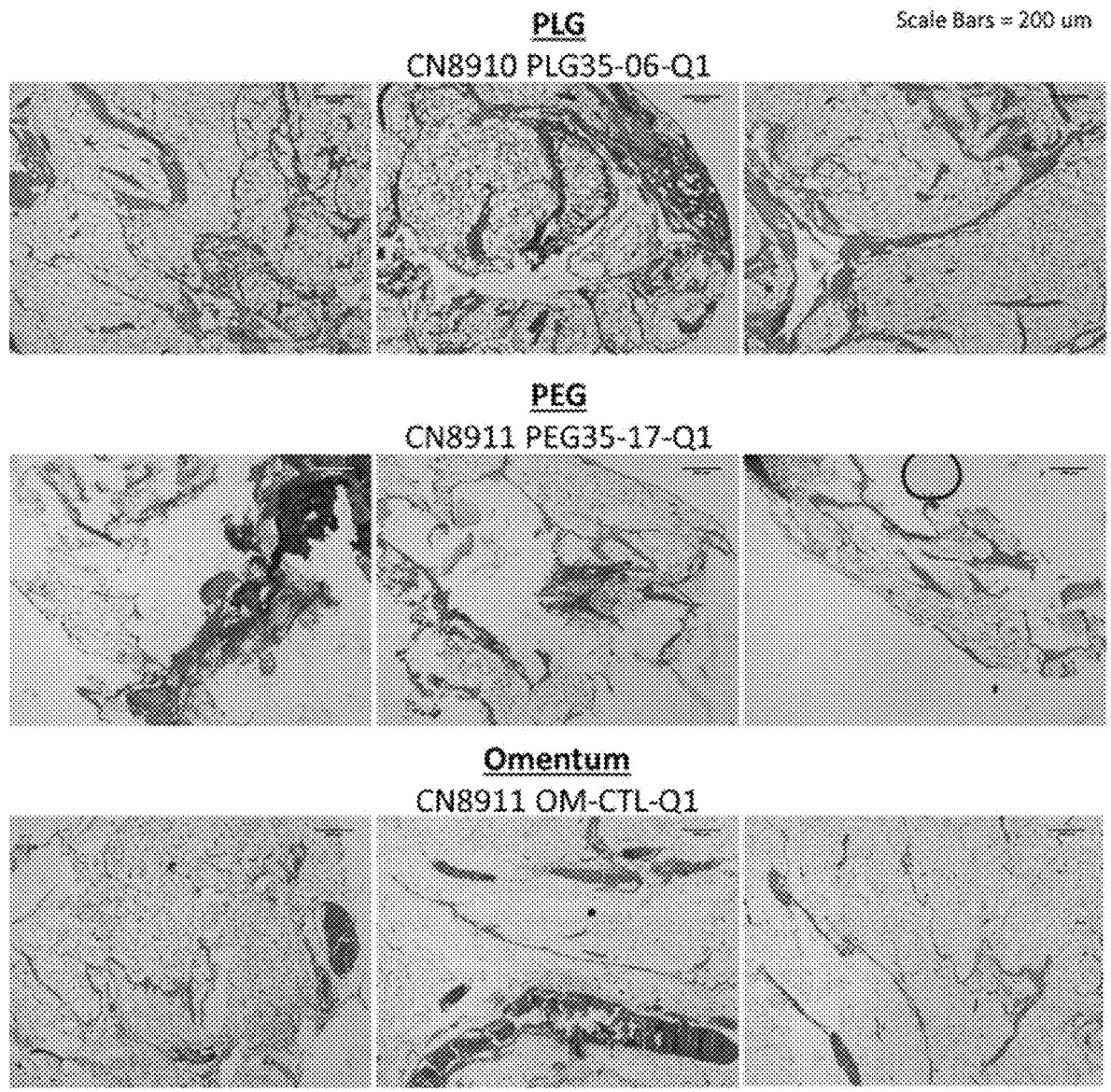
FIG. 25 shows hemotoxylin and eosin staining of PLG scaffolds, PEG scaffolds, and omentum from the immunoreactivity study described in Example 8. Scaffolds, transplanted without any islets, and omentum were removed from NHP 30 days following transplantation and stained with hemotoxylin and eosin. Scale bars=200 µm.
Figure 26:
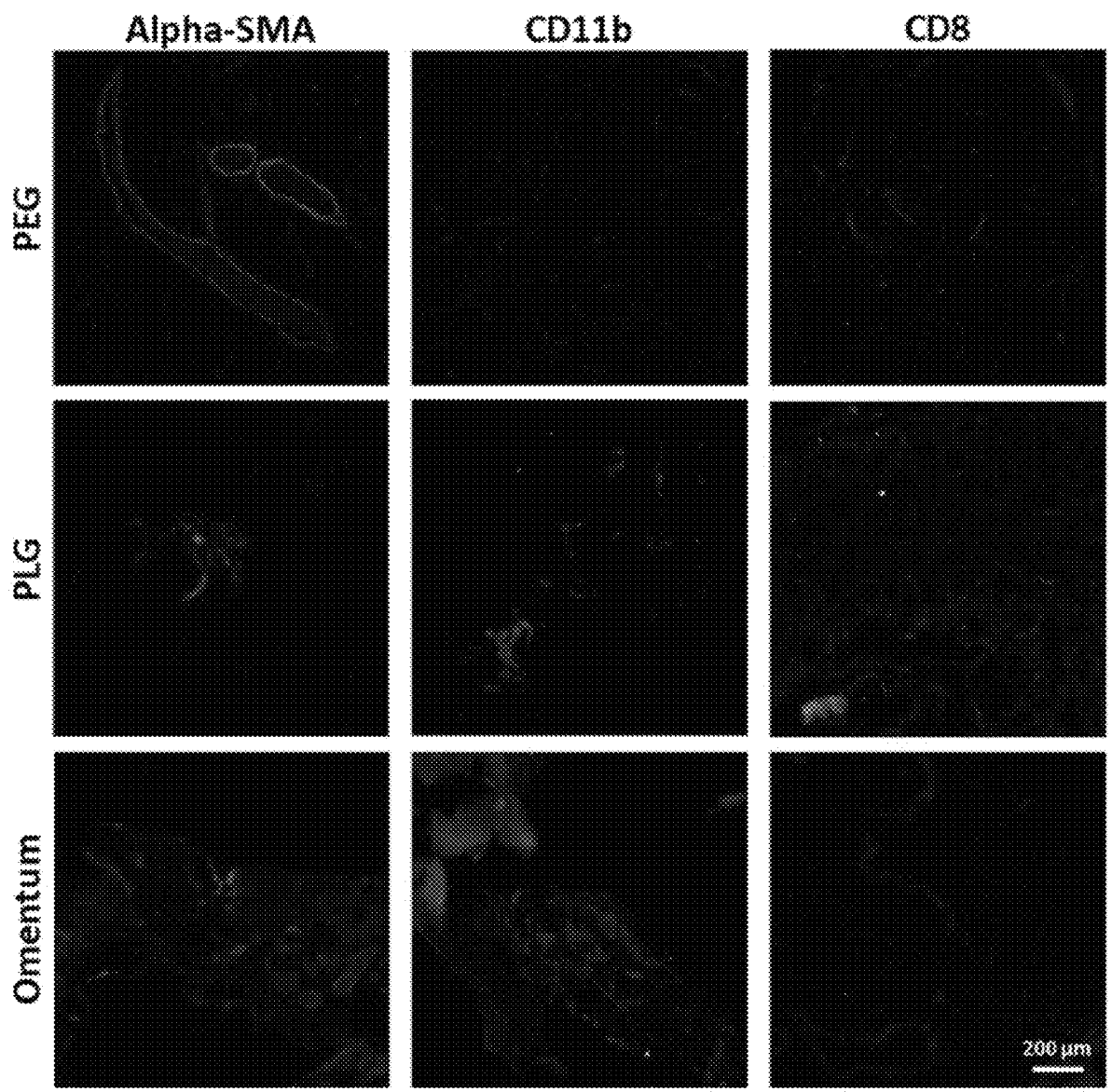
FIG. 26 shows immunohistochemistry staining for immune markers of PLG scaffolds, PEG scaffolds, and omentum from the immunoreactivity study described in Example 8. Scaffolds, transplanted without any islets, and omentum were removed from NHP 30 days following transplantation and stained for alpha-smooth muscle actin (red), CD11b (green) CD8 (yellow), and nuclear counterstain with DAPI (blue). Scale bar=200 µm.

Transplantation of Allogeneic Islets Seeded to PEG Scaffolds to Non-Human Primate Model In this example, the microporous PEG scaffolds were scaled up in size (35 mm diameter) for islet transplantation to the omentum of non-human primate (NHP) models. These studies were conducted under GMP conditions, in anticipation for clinical testing of microporous PEG scaffolds for extrahepatic islet transplantation. Standard operating procedures have been developed for the fabrication of PEG scaffolds under GMP conditions, including packaging and sterilization of scaffolds using gamma irradiation. Toxicology panels have been conducted on the sterilized PEG scaffolds and have determined that these scaffolds contain no bacterial, viral, or fungal contamination and possess endotoxin levels well below acceptable thresholds. These PEG scaffolds were first transplanted to the omentum of NHPs without the seeding of islets for a 30-day immunoreactivity study (FIG. 24). After 30 days, scaffolds were removed and histology was conducted to examine the explanted scaffolds for immune markers and inflammatory response, such as fibrosis. Hemotoxylin and eosin staining (FIG. 25) indicated that PEG scaffolds had less fibrosis than PLG scaffolds and immunohistochemistry for immune markers (FIG. 26) demonstrated less immune cell infiltration within PEG scaffolds compared to PLG scaffolds. Thus, is was found that in primates, the foreign body/immune response to the PEG scaffold was milder compared with the PLG scaffold. This property of the PEG scaffold improves the engraftment of transplanted cells, and thus, the effectiveness of the transplant.

Figure 27:
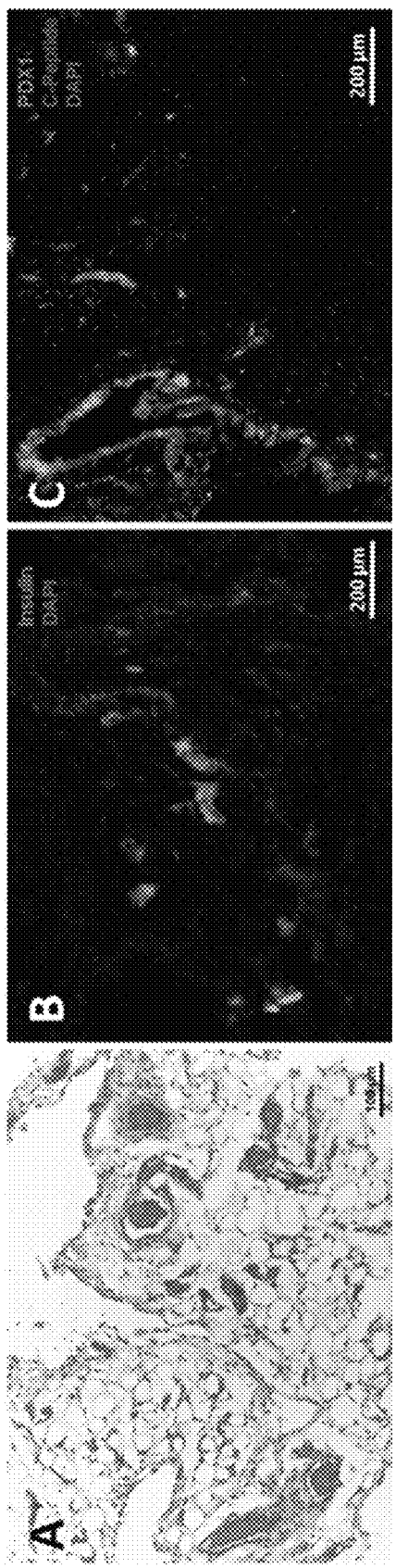
FIG. 27 depicts results from a scaffold transplantation, wherein the scaffold was seeded with allogeneic islets, to the bursa omentalis of a non-diabetic NHP for a 30 day study. Thirty days following transplantation of PEG scaffolds seeded with allogeneic islets, the scaffolds were removed and histological staining was conducted. Hemotoxylin and eosin staining of PEG scaffold seeded with allogeneic islets (A), immunohistochemistry staining for insulin (green) and nuclear counterstain with DAPI (blue) (B), and immunohistochemistry staining for PDX1 (green), C-Peptide (red), and nuclear counterstain with DAPI (blue) (C).

Another transplant was conducted where allogeneic NHP islets were transplanted to a non-diabetic NHP for a 30 day study. An incision was made into the omentum of a NHP to create a pocket in which a scaffold, seeded with allogeneic islets, was inserted, then wrapped in the omental tissue. Following 30 days, scaffolds were removed and histology was conducted (FIG. 27), which indicated the presence of insulin-producing islets within the PEG scaffolds. Further studies using PEG scaffolds seeded with allogeneic islets to a diabetic NHP will evaluate the function of transplanted islets seeded to PEG scaffolds.

The microporous scaffolds of various embodiments provide a predefined structure that is easily loaded with islets and/or hESC-derived n-cell progenitors and readily handled by a surgeon for subcutaneous implantation into a patient, for example, into the omentum. The porous structure of the scaffolds allows for adhesion to fat tissue, and thus avoids significant manipulation to the fat pad. The microporous platform supports the efficient transplantation, engraftment, and function of transplanted islets. And advantageously, PEG-based microporous scaffolds have a decreased inflammatory response relative to PLG, have mechanical properties that are a better match with the omentum, and can be made non-degradable thereby allowing retrieval if needed. Furthermore, PEG is highly biocompatible and has been widely used in numerous biomedical applications.

For islet transplantation embodiments, islets loaded on the scaffold are localized in the outer portion of the scaffold and implantation places these cells adjacent to the host tissue. Host tissue can readily infiltrate into the pores and revascularize the islets. The modification with collagen IV can enhance islet survival and function post-transplantation through decreased apoptosis, increased glucose stimulated insulin secretion, and increased metabolic activity. The combination of factors to promote islet survival combined with revascularization minimizes the islet mass necessary to normalize blood glucose levels. For β-cell progenitors, the microporous scaffolds are also adapted to deliver angiogenic or trophic factors that enhance their maturation toward β-cells.

Taken together, the microporous scaffolds disclosed herein provide a platform that consists of an architecture to maximize engraftment and transplantation, along with the ability to deliver virtually any protein or small molecule over pre-defined time scales of days to weeks into that microenvironment. This combination of structure and biologic signals maximizes function of transplanted islets, while minimizing the inflammatory response that can hinder engraftment.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention. The foregoing description is given for clearness of understanding; and no unnecessary limitations should be understood therefrom, as modifications within the scope of the invention may be apparent to those having ordinary skill in the art.

What is claimed is:

1. A biomaterial implant comprising a microporous scaffold comprising poly(ethylene glycol) (PEG) or poly(lactide-co-glycolide) (PLG), wherein prior to implantation, the scaffold comprises about 5 million or more β-cell progenitors per $cm^2$, wherein the β-cell progenitors are (i) located in pores of the scaffold and (ii) not encapsulated.

2. The biomaterial implant of claim 1 which further comprises vascular endothelial growth factor (VEGF) or a trophic factor.

3. The biomaterial implant of claim 2, wherein the trophic factor is exendin-4.

4. The biomaterial implant of claim 1, wherein average pore size in the scaffold are from about 250 to about 600 micrometers (μm).

5. A method of treating Type 1 diabetes in a subject in need thereof, comprising implanting the biomaterial implant of claim 1 into the subject.

6. The method of claim 5, wherein the biomaterial implant is subcutaneously implanted into the subject, optionally, into the omentum of the subject.

7. The biomaterial implant of claim 1, wherein the β-cell progenitors are derived from pluripotent stem cells.

8. The biomaterial implant of claim 1, wherein the β-cell progenitors are self-assembled into islet-like clusters within pores of the scaffold prior to implantation.

9. The biomaterial implant of claim 4, wherein the scaffold comprises PEG and the average pore size of the pores of the scaffold is about 500 μm to about 600 μm.

10. The biomaterial implant of claim 8, wherein prior to implantation the islet-like clusters express markers of mature β cells and/or produce insulin.

11. The biomaterial implant of claim 8, wherein prior to implantation the islet-like clusters express markers of mature β cells and produce insulin.

12. The biomaterial implant of claim 10, wherein the markers are Pdx1, Sur1, Kir2, insulin, glucagon, MafA, Onecut1, NGN3, Nkx2.2, Nkx6.1, Neuro D, Msx2, SUR1, KIR6.2, or a combination thereof.

13. The biomaterial implant of claim 11, wherein the markers are Pdx1, Sur1, Kir2, insulin, glucagon, MafA, Onecut1, NGN3, Nkx2.2, Nkx6.1, Neuro D, Msx2, SUR1, KIR6.2, or a combination thereof.

* * * * *

UNITED STATES PATENT AND TRADEMARK OFFICE
CERTIFICATE OF CORRECTION

PATENT NO. : 10,973,956 B2
APPLICATION NO. : 15/863843
DATED : April 13, 2021
INVENTOR(S) : Tadas Kasputis et al.

It is certified that error appears in the above-identified patent and that said Letters Patent is hereby corrected as shown below:

In the Claims

At Column 29, Line 23, "Msx2, SUR1," should be -- Msx2, --.

At Column 29, Line 27, "Msx2, SUR1," should be -- Msx2, --.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*